United States Patent
Johnson et al.

(10) Patent No.: US 10,758,315 B2
(45) Date of Patent: Sep. 1, 2020

(54) METHOD AND SYSTEM FOR IMPROVING 2D-3D REGISTRATION CONVERGENCE

(71) Applicant: GLOBUS MEDICAL, INC., Audubon, PA (US)

(72) Inventors: Norbert Johnson, North Andover, MA (US); Neil Crawford, Chandler, AZ (US); Jeffrey Forsyth, Cranston, RI (US); Yuan Cheng, Andover, MA (US); Jawad Mokhtar, Carlisle, MA (US)

(73) Assignee: Globus Medical Inc., Audubon, PA (US)

( * ) Notice: Subject to any disclaimer, the term of this patent is extended or adjusted under 35 U.S.C. 154(b) by 756 days.

(21) Appl. No.: 15/289,537

(22) Filed: Oct. 10, 2016

(65) Prior Publication Data

US 2017/0020630 A1    Jan. 26, 2017

Related U.S. Application Data

(63) Continuation-in-part of application No. 15/157,444, filed on May 18, 2016, which is a continuation-in-part
(Continued)

(51) Int. Cl.
*A61B 90/00* (2016.01)
*A61B 34/30* (2016.01)
(Continued)

(52) U.S. Cl.
CPC ............ *A61B 90/39* (2016.02); *A61B 5/064* (2013.01); *A61B 34/20* (2016.02); *A61B 34/30* (2016.02);
(Continued)

(58) Field of Classification Search
CPC ......... A61B 90/96; A61B 90/98; A61B 34/20; A61B 90/39; A61B 34/30; A61B 5/064;
(Continued)

(56) References Cited

U.S. PATENT DOCUMENTS

| | | | |
|---|---|---|---|
| 4,150,293 | A | 4/1979 | Franke |
| 5,020,933 | A | 6/1991 | Salvestro et al. |

(Continued)

FOREIGN PATENT DOCUMENTS

| | | | |
|---|---|---|---|
| EP | 1103223 A2 | 5/2001 | |
| EP | 1346687 A1 | 9/2003 | |

(Continued)

OTHER PUBLICATIONS

Marintschev et al.: "Navigation of vertebro-pelvic fixations based on CT-fluoro macthing", European Spine Journal, Springer, Berlin, DE, vol. 19, No. 11, pp. 1921-1927, Jun. 16, 2010.
(Continued)

*Primary Examiner* — Oommen Jacob

(57) ABSTRACT

A method for registration of digital medical images is provided. The method includes the step of storing a 3D digital medical image having a 3D anatomical feature and a first coordinate system and storing a 2D digital medical image having a 2D anatomical feature and a second coordinate system. The method further includes the steps of storing a placement of a digital medical object on the 3D digital medical image and the 2D digital medical image and generating a simulated 2D digital medical image from the 3D digital medical image, wherein the simulated 2D digital medical image comprises a simulated 2D anatomical feature corresponding to the 3D anatomical feature. The 2D anatomical feature is compared with the simulated 2D anatomical feature until a match is reached and a registration of the first coordinate system with the second coordinate system based on the match is determined.

20 Claims, 15 Drawing Sheets

Related U.S. Application Data of application No. 15/095,883, filed on Apr. 11, 2016, which is a continuation-in-part of application No. 14/062,707, filed on Oct. 24, 2013, which is a continuation-in-part of application No. 13/924,505, filed on Jun. 21, 2013, now Pat. No. 9,782,229.

(60) Provisional application No. 61/800,527, filed on Mar. 15, 2013, provisional application No. 61/662,702, filed on Jun. 21, 2012.

(51) Int. Cl.

| | | |
|---|---|---|
| *A61B 5/06* | (2006.01) | |
| *A61B 90/96* | (2016.01) | |
| *G06T 7/30* | (2017.01) | |
| *A61B 34/20* | (2016.01) | |
| *A61B 90/98* | (2016.01) | |
| *A61B 90/11* | (2016.01) | |
| *A61B 17/17* | (2006.01) | |
| *A61B 17/00* | (2006.01) | |

(52) U.S. Cl.
CPC ............ *A61B 90/361* (2016.02); *A61B 90/96* (2016.02); *A61B 90/98* (2016.02); *G06T 7/30* (2017.01); *A61B 17/17* (2013.01); *A61B 90/11* (2016.02); *A61B 2017/00876* (2013.01); *A61B 2034/2051* (2016.02); *A61B 2034/2055* (2016.02); *A61B 2034/2057* (2016.02); *A61B 2034/2065* (2016.02); *A61B 2034/2072* (2016.02); *A61B 2090/034* (2016.02); *A61B 2090/0811* (2016.02); *A61B 2090/3937* (2016.02); *A61B 2090/3945* (2016.02); *G06T 2207/10004* (2013.01); *G06T 2207/10012* (2013.01); *G06T 2207/10081* (2013.01); *G06T 2207/10088* (2013.01); *G06T 2207/30204* (2013.01)

(58) Field of Classification Search
CPC .................. A61B 90/361; A61B 17/17; A61B 2017/00876; A61B 90/11; A61B 2090/034; A61B 2090/0811; A61B 2034/2055; A61B 2034/2057; A61B 2034/2072; A61B 2090/3945; A61B 2034/2051; A61B 2090/3937; A61B 2034/2065; G06T 7/30; G06T 2207/10081; G06T 2207/10088; G06T 2207/10012; G06T 2207/10004; G06T 2207/30204
USPC ................................................ 600/424, 407
See application file for complete search history.

(56) References Cited

U.S. PATENT DOCUMENTS

| | | | |
|---|---|---|---|
| 5,246,010 A | 9/1993 | Gazzara et al. | |
| 5,598,453 A | 1/1997 | Baba et al. | |
| 5,772,594 A | 6/1998 | Barrick | |
| 5,951,475 A * | 9/1999 | Gueziec | G06T 3/0068 128/922 |
| 5,987,960 A | 11/1999 | Messner et al. | |
| 5,999,840 A * | 12/1999 | Grimson | G06T 3/0068 600/424 |
| 6,031,888 A | 2/2000 | Ivan et al. | |
| 6,069,932 A * | 5/2000 | Peshkin | A61B 6/464 378/42 |
| 6,144,875 A | 11/2000 | Schweikard et al. | |
| 6,203,196 B1 | 3/2001 | Meyer et al. | |
| 6,301,495 B1 * | 10/2001 | Gueziec | A61B 6/00 600/407 |
| 6,306,126 B1 | 10/2001 | Montezuma | |
| 6,314,311 B1 | 11/2001 | Williams et al. | |
| 6,320,929 B1 | 11/2001 | Von Der Haar | |
| 6,477,400 B1 | 11/2002 | Barrick | |
| 6,484,049 B1 | 11/2002 | Seeley et al. | |
| 6,487,267 B1 | 11/2002 | Wolter | |
| 6,490,475 B1 | 12/2002 | Seeley et al. | |
| 6,501,981 B1 | 12/2002 | Schweikard et al. | |
| 6,535,756 B1 | 3/2003 | Simon et al. | |
| 6,614,453 B1 | 9/2003 | Suri et al. | |
| 6,614,871 B1 | 9/2003 | Kobiki et al. | |
| 6,619,840 B2 | 9/2003 | Rasche et al. | |
| 6,640,128 B2 * | 10/2003 | Vilsmeier | A61C 1/084 433/215 |
| 6,666,579 B2 | 12/2003 | Jensen | |
| 6,725,080 B2 * | 4/2004 | Melkent | A61B 5/06 600/424 |
| 6,757,068 B2 | 6/2004 | Foxlin | |
| 6,782,287 B2 | 8/2004 | Grzeszczuk et al. | |
| 6,856,826 B2 | 2/2005 | Seeley et al. | |
| 6,856,827 B2 | 2/2005 | Seeley et al. | |
| 6,920,347 B2 | 7/2005 | Simon et al. | |
| 6,922,632 B2 | 7/2005 | Foxlin | |
| 6,988,009 B2 | 1/2006 | Grimm et al. | |
| 6,996,487 B2 | 2/2006 | Jutras et al. | |
| 7,016,457 B1 | 3/2006 | Senzig et al. | |
| 7,043,961 B2 | 5/2006 | Pandey et al. | |
| 7,062,006 B1 | 6/2006 | Pelc et al. | |
| 7,063,705 B2 | 6/2006 | Young et al. | |
| 7,072,707 B2 | 7/2006 | Galloway, Jr. et al. | |
| 7,099,428 B2 | 8/2006 | Clinthorne et al. | |
| 7,108,421 B2 | 9/2006 | Gregerson et al. | |
| 7,130,676 B2 | 10/2006 | Barrick | |
| 7,139,418 B2 | 11/2006 | Abovitz et al. | |
| 7,194,120 B2 | 3/2007 | Wicker et al. | |
| 7,197,107 B2 | 3/2007 | Arai et al. | |
| 7,207,995 B1 | 4/2007 | Vandewalle | |
| 7,231,014 B2 | 6/2007 | Levy | |
| 7,231,063 B2 | 6/2007 | Naimark et al. | |
| 7,301,648 B2 | 11/2007 | Foxlin | |
| 7,313,430 B2 | 12/2007 | Urquhart et al. | |
| 7,318,805 B2 | 1/2008 | Schweikard et al. | |
| 7,324,623 B2 | 1/2008 | Heuscher et al. | |
| 7,327,865 B2 | 2/2008 | Fu et al. | |
| 7,460,637 B2 | 12/2008 | Clinthorne et al. | |
| 7,493,153 B2 | 2/2009 | Ahmed et al. | |
| 7,505,617 B2 | 3/2009 | Fu et al. | |
| 7,606,613 B2 * | 10/2009 | Simon | A61B 34/20 600/426 |
| 7,623,902 B2 | 11/2009 | Pacheco | |
| 7,643,862 B2 | 1/2010 | Schoenefeld | |
| 7,661,881 B2 | 2/2010 | Gregerson et al. | |
| 7,683,331 B2 | 3/2010 | Chang | |
| 7,683,332 B2 | 3/2010 | Chang | |
| 7,702,379 B2 | 4/2010 | Avinash et al. | |
| 7,702,477 B2 | 4/2010 | Tuemmler et al. | |
| 7,711,083 B2 | 5/2010 | Heigl et al. | |
| 7,712,961 B2 * | 5/2010 | Horndler | A61B 6/12 378/207 |
| 7,725,253 B2 | 5/2010 | Foxlin | |
| 7,726,171 B2 | 6/2010 | Langlotz et al. | |
| 7,760,849 B2 | 7/2010 | Zhang | |
| 7,796,728 B2 | 9/2010 | Bergfjord | |
| 7,813,838 B2 | 10/2010 | Sommer | |
| 7,835,778 B2 | 11/2010 | Foley et al. | |
| 7,835,784 B2 | 11/2010 | Mire et al. | |
| 7,840,256 B2 | 11/2010 | Lakin et al. | |
| 7,844,320 B2 | 11/2010 | Shahidi | |
| 7,853,305 B2 | 12/2010 | Simon et al. | |
| 7,853,313 B2 | 12/2010 | Thompson | |
| 7,900,524 B2 | 3/2011 | Calloway et al. | |
| 7,940,999 B2 | 5/2011 | Liao et al. | |
| 7,945,012 B2 | 5/2011 | Ye et al. | |
| 7,945,021 B2 | 5/2011 | Shapiro et al. | |
| 8,019,045 B2 | 9/2011 | Kato | |
| 8,021,310 B2 | 9/2011 | Sanborn et al. | |
| 8,052,688 B2 | 11/2011 | Wolf, II | |
| 8,086,299 B2 | 12/2011 | Adler et al. | |
| 8,098,914 B2 | 1/2012 | Liao et al. | |

(56) References Cited

U.S. PATENT DOCUMENTS

| | | | |
|---|---|---|---|
| 8,100,950 B2 | 1/2012 | St. Clair et al. | |
| 8,116,430 B1 | 2/2012 | Shapiro et al. | |
| 8,121,249 B2 | 2/2012 | Wang et al. | |
| 8,150,494 B2 | 4/2012 | Simon et al. | |
| 8,208,708 B2 | 6/2012 | Homan et al. | |
| 8,224,024 B2 | 7/2012 | Foxlin et al. | |
| 8,238,625 B2* | 8/2012 | Strommer | G06K 9/32 |
| | | | 382/128 |
| 8,311,611 B2 | 11/2012 | Csavoy et al. | |
| 8,313,430 B1 | 11/2012 | Pimenta | |
| 8,335,557 B2 | 12/2012 | Maschke | |
| 8,358,818 B2 | 1/2013 | Miga et al. | |
| 8,379,791 B2 | 2/2013 | Forthmann et al. | |
| 8,386,019 B2 | 2/2013 | Camus et al. | |
| 8,394,099 B2 | 3/2013 | Patwardhan | |
| 8,462,911 B2 | 6/2013 | Vesel et al. | |
| 8,526,700 B2 | 9/2013 | Isaacs | |
| 8,541,970 B2 | 9/2013 | Nowlin et al. | |
| 8,560,118 B2 | 10/2013 | Green et al. | |
| 8,597,198 B2 | 12/2013 | Sanborn et al. | |
| 8,611,985 B2 | 12/2013 | Lavallee et al. | |
| 8,630,389 B2 | 1/2014 | Kato | |
| 8,634,897 B2 | 1/2014 | Simon et al. | |
| 8,660,635 B2 | 2/2014 | Simon et al. | |
| 8,678,647 B2 | 3/2014 | Gregerson et al. | |
| 8,696,458 B2 | 4/2014 | Foxlin et al. | |
| 8,706,185 B2 | 4/2014 | Foley et al. | |
| 8,727,618 B2 | 5/2014 | Maschke et al. | |
| 8,738,115 B2 | 5/2014 | Amberg et al. | |
| 8,740,882 B2 | 6/2014 | Jun et al. | |
| 8,781,186 B2 | 7/2014 | Clements et al. | |
| 8,781,630 B2 | 7/2014 | Banks et al. | |
| 8,787,520 B2 | 7/2014 | Baba | |
| 8,792,704 B2 | 7/2014 | Isaacs | |
| 8,798,231 B2 | 8/2014 | Notohara et al. | |
| 8,812,077 B2 | 8/2014 | Dempsey | |
| 8,814,793 B2 | 8/2014 | Brabrand | |
| 8,818,105 B2 | 8/2014 | Myronenko et al. | |
| 8,821,511 B2 | 9/2014 | Von Jako et al. | |
| 8,867,703 B2 | 10/2014 | Shapiro et al. | |
| 8,888,821 B2 | 11/2014 | Rezach et al. | |
| 8,964,934 B2 | 2/2015 | Ein-Gal | |
| 8,992,580 B2 | 3/2015 | Bar et al. | |
| 8,996,169 B2 | 3/2015 | Lightcap et al. | |
| 9,001,963 B2 | 4/2015 | Sowards-Emmerd et al. | |
| 9,002,076 B2 | 4/2015 | Khadem et al. | |
| 9,044,190 B2 | 6/2015 | Rubner et al. | |
| 9,107,683 B2 | 8/2015 | Hourtash et al. | |
| 9,119,670 B2* | 9/2015 | Yang | A61B 5/055 |
| 9,125,556 B2 | 9/2015 | Zehavi et al. | |
| 9,131,986 B2 | 9/2015 | Greer et al. | |
| 9,215,968 B2 | 12/2015 | Schostek et al. | |
| 9,308,050 B2 | 4/2016 | Kostrzewski et al. | |
| 9,380,984 B2 | 7/2016 | Li et al. | |
| 9,393,039 B2 | 7/2016 | Lechner et al. | |
| 9,398,886 B2 | 7/2016 | Gregerson et al. | |
| 9,398,890 B2 | 7/2016 | Dong et al. | |
| 9,414,859 B2 | 8/2016 | Ballard et al. | |
| 9,420,975 B2 | 8/2016 | Gutfleisch et al. | |
| 9,492,235 B2 | 11/2016 | Hourtash et al. | |
| 9,592,096 B2 | 3/2017 | Maillet et al. | |
| 9,750,465 B2 | 9/2017 | Engel et al. | |
| 9,757,203 B2 | 9/2017 | Hourtash et al. | |
| 9,795,354 B2 | 10/2017 | Menegaz et al. | |
| 9,814,535 B2 | 11/2017 | Bar et al. | |
| 9,820,783 B2 | 11/2017 | Donner et al. | |
| 9,833,265 B2 | 12/2017 | Donner et al. | |
| 9,848,922 B2 | 12/2017 | Tohmeh et al. | |
| 9,925,011 B2 | 3/2018 | Gombert et al. | |
| 9,931,025 B1 | 4/2018 | Graetzel et al. | |
| 9,943,707 B2* | 4/2018 | Maurer, Jr. | G06T 7/0014 |
| 10,034,717 B2 | 7/2018 | Miller et al. | |
| 10,173,078 B2* | 1/2019 | Maurer, Jr. | G06T 7/0014 |
| 2001/0036302 A1 | 11/2001 | Miller | |
| 2003/0029464 A1* | 2/2003 | Chen | A61B 90/36 |
| | | | 600/429 |
| 2003/0073901 A1* | 4/2003 | Simon | G06F 19/00 |
| | | | 600/424 |
| 2003/0130576 A1* | 7/2003 | Seeley | A61B 6/12 |
| | | | 600/426 |
| 2004/0076259 A1 | 4/2004 | Jensen et al. | |
| 2004/0077939 A1* | 4/2004 | Graumann | A61B 6/547 |
| | | | 600/424 |
| 2004/0102698 A1* | 5/2004 | Vilsmeier | A61B 5/06 |
| | | | 600/424 |
| 2004/0111024 A1* | 6/2004 | Zheng | A61B 6/4441 |
| | | | 600/426 |
| 2005/0015005 A1* | 1/2005 | Kockro | A61B 90/36 |
| | | | 600/427 |
| 2005/0027193 A1* | 2/2005 | Mitschke | A61B 6/12 |
| | | | 600/427 |
| 2005/0085718 A1* | 4/2005 | Shahidi | A61B 1/04 |
| | | | 600/424 |
| 2005/0149045 A1 | 7/2005 | Elliott | |
| 2005/0215888 A1 | 9/2005 | Grimm et al. | |
| 2006/0178559 A1 | 8/2006 | Kumar et al. | |
| 2006/0184396 A1 | 8/2006 | Dennis et al. | |
| 2006/0291612 A1 | 12/2006 | Nishide et al. | |
| 2007/0038059 A1 | 2/2007 | Sheffer et al. | |
| 2007/0073133 A1 | 3/2007 | Schoenefeld | |
| 2007/0122020 A1 | 5/2007 | Claus et al. | |
| 2007/0127801 A1* | 6/2007 | Kalke | G06T 11/006 |
| | | | 382/131 |
| 2008/0004523 A1 | 1/2008 | Jensen | |
| 2008/0013809 A1 | 1/2008 | Zhu et al. | |
| 2008/0033410 A1* | 2/2008 | Rastegar | A61B 18/20 |
| | | | 606/9 |
| 2008/0082109 A1 | 4/2008 | Moll et al. | |
| 2008/0108991 A1 | 5/2008 | Von Jako | |
| 2008/0144906 A1 | 6/2008 | Allred et al. | |
| 2008/0154389 A1 | 6/2008 | Smith et al. | |
| 2008/0161680 A1 | 7/2008 | Von Jako et al. | |
| 2008/0188934 A1 | 8/2008 | Moser et al. | |
| 2008/0200794 A1 | 8/2008 | Teichman et al. | |
| 2008/0235052 A1 | 9/2008 | Node-Langlois et al. | |
| 2008/0242978 A1* | 10/2008 | Simon | A61B 90/36 |
| | | | 600/426 |
| 2008/0269596 A1 | 10/2008 | Revie et al. | |
| 2008/0287781 A1 | 11/2008 | Revie et al. | |
| 2008/0300477 A1 | 12/2008 | Lloyd et al. | |
| 2008/0302950 A1 | 12/2008 | Park et al. | |
| 2008/0306490 A1 | 12/2008 | Lakin et al. | |
| 2008/0319311 A1 | 12/2008 | Hamadeh | |
| 2009/0080737 A1* | 3/2009 | Battle | A61M 25/0662 |
| | | | 382/131 |
| 2009/0088773 A1* | 4/2009 | Zhao | G06K 9/3241 |
| | | | 606/130 |
| 2009/0099445 A1 | 4/2009 | Burger | |
| 2009/0129650 A1* | 5/2009 | Hawkes | G06T 7/344 |
| | | | 382/131 |
| 2009/0177081 A1* | 7/2009 | Joskowicz | A61B 34/20 |
| | | | 600/426 |
| 2009/0185655 A1 | 7/2009 | Koken et al. | |
| 2009/0198121 A1 | 8/2009 | Hoheisel | |
| 2009/0306480 A1 | 12/2009 | Protopsaltis | |
| 2010/0022874 A1 | 1/2010 | Wang et al. | |
| 2010/0039506 A1 | 2/2010 | Sarvestani et al. | |
| 2010/0046718 A1 | 2/2010 | Weiser et al. | |
| 2010/0125286 A1 | 5/2010 | Wang et al. | |
| 2010/0168763 A1* | 7/2010 | Zhao | A61B 34/30 |
| | | | 606/130 |
| 2010/0174410 A1 | 7/2010 | Greer et al. | |
| 2010/0228117 A1 | 9/2010 | Hartmann | |
| 2010/0274120 A1 | 10/2010 | Heuscher | |
| 2010/0296723 A1* | 11/2010 | Greer | A61B 90/36 |
| | | | 382/153 |
| 2011/0040305 A1 | 2/2011 | Gomez et al. | |
| 2011/0098553 A1 | 4/2011 | Robbins et al. | |
| 2011/0184245 A1 | 7/2011 | Xia et al. | |
| 2011/0188639 A1* | 8/2011 | Cooke | A61B 6/025 |
| | | | 378/208 |

(56) References Cited

U.S. PATENT DOCUMENTS

| | | |
|---|---|---|
| 2011/0190588 A1 | 8/2011 | McKay |
| 2011/0282189 A1 | 11/2011 | Graumann |
| 2011/0286573 A1 | 11/2011 | Schretter et al. |
| 2011/0319941 A1* | 12/2011 | Bar .................... A61B 17/1671 606/279 |
| 2012/0035507 A1 | 2/2012 | George et al. |
| 2012/0051498 A1 | 3/2012 | Koishi |
| 2012/0063564 A1* | 3/2012 | Klingenbeck .......... A61B 6/032 378/4 |
| 2012/0143084 A1 | 6/2012 | Shoham |
| 2012/0150505 A1* | 6/2012 | Couch .................... A61B 6/583 703/2 |
| 2012/0179026 A1* | 7/2012 | Simon .................... A61B 90/36 600/411 |
| 2012/0226145 A1 | 9/2012 | Chang et al. |
| 2012/0235909 A1 | 9/2012 | Birkenbach et al. |
| 2012/0289820 A1 | 11/2012 | Rohling |
| 2012/0294498 A1 | 11/2012 | Popovic |
| 2013/0016889 A1 | 1/2013 | Myronenko et al. |
| 2013/0018384 A1* | 1/2013 | Kappel ............ A61B 17/32056 606/111 |
| 2013/0051647 A1* | 2/2013 | Miao ...................... G06T 7/344 382/132 |
| 2013/0060146 A1 | 3/2013 | Yang et al. |
| 2013/0094742 A1 | 4/2013 | Feilkas |
| 2013/0113791 A1 | 5/2013 | Isaacs et al. |
| 2013/0165937 A1 | 6/2013 | Patwardhan |
| 2013/0184873 A1 | 7/2013 | Namiki |
| 2013/0281821 A1 | 10/2013 | Liu et al. |
| 2013/0307955 A1 | 11/2013 | Deitz et al. |
| 2013/0342578 A1 | 12/2013 | Isaacs |
| 2013/0345757 A1 | 12/2013 | Stad |
| 2014/0046132 A1 | 2/2014 | Hoeg et al. |
| 2014/0049629 A1 | 2/2014 | Siewerdsen et al. |
| 2014/0052150 A1 | 2/2014 | Taylor et al. |
| 2014/0080086 A1 | 3/2014 | Chen |
| 2014/0096369 A1 | 4/2014 | Matsumoto et al. |
| 2014/0121676 A1 | 5/2014 | Kostrzewski et al. |
| 2014/0135744 A1 | 5/2014 | Stein et al. |
| 2014/0135796 A1 | 5/2014 | Simon et al. |
| 2014/0200587 A1 | 7/2014 | Pompee et al. |
| 2014/0130810 A1 | 8/2014 | Azizian et al. |
| 2014/0221819 A1 | 8/2014 | Sarment |
| 2014/0221822 A1 | 8/2014 | Ehlers et al. |
| 2014/0228631 A1 | 8/2014 | Kwak et al. |
| 2014/0234804 A1 | 8/2014 | Huang et al. |
| 2014/0275955 A1* | 9/2014 | Crawford ............... A61B 5/062 600/409 |
| 2014/0336669 A1 | 11/2014 | Park |
| 2014/0343416 A1 | 11/2014 | Panescu et al. |
| 2014/0371577 A1 | 12/2014 | Mallet et al. |
| 2015/0039034 A1 | 2/2015 | Frankel et al. |
| 2015/0085970 A1 | 3/2015 | Bouhnik et al. |
| 2015/0100066 A1* | 4/2015 | Kostrzewski .......... A61B 34/30 606/130 |
| 2015/0146847 A1 | 5/2015 | Liu |
| 2015/0150524 A1 | 6/2015 | Yorkston et al. |
| 2015/0196261 A1 | 7/2015 | Funk |
| 2015/0196365 A1 | 7/2015 | Kostrzewski et al. |
| 2015/0209056 A1 | 7/2015 | Shoham et al. |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0220320 A1* | 8/2016 | Crawford ............... A61B 34/30 |
| 2016/0235480 A1 | 8/2016 | Scholl et al. |
| 2016/0235493 A1 | 8/2016 | Leboeuf, II et al. |
| 2016/0242849 A9* | 8/2016 | Crawford ............... A61B 34/74 |
| 2016/0249990 A1 | 9/2016 | Glozman et al. |
| 2016/0256225 A1* | 9/2016 | Crawford ............... A61B 34/32 |
| 2016/0296266 A1 | 10/2016 | Chandanson et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0020630 A1* | 1/2017 | Johnson ................. A61B 90/96 |
| 2017/0079727 A1 | 3/2017 | Crawford et al. |
| 2017/0112552 A1 | 4/2017 | Sinnott et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0231713 A1* | 8/2017 | Siewerdsen ........... A61B 90/36 382/128 |
| 2017/0243361 A1* | 8/2017 | Schaffert ................. G06T 7/564 |
| 2017/0258426 A1 | 9/2017 | Risher-Kelly et al. |
| 2017/0258526 A1 | 9/2017 | Lang |
| 2017/0258535 A1 | 9/2017 | Crawford et al. |
| 2017/0265952 A1 | 9/2017 | Donhowe et al. |
| 2017/0273748 A1 | 9/2017 | Hourtash et al. |
| 2017/0296277 A1 | 10/2017 | Hourtash et al. |
| 2017/0312032 A1 | 11/2017 | Amanatullah et al. |
| 2017/0348061 A1 | 12/2017 | Joshi et al. |
| 2017/0360493 A1 | 12/2017 | Zucher et al. |
| 2018/0021597 A1* | 1/2018 | Berlinger ............. A61N 5/1049 600/1 |
| 2018/0042464 A1 | 2/2018 | Arai et al. |
| 2018/0200016 A1 | 7/2018 | Chappuis |

FOREIGN PATENT DOCUMENTS

| | | |
|---|---|---|
| EP | 1523950 A1 | 4/2005 |
| EP | 2471483 A1 | 7/2012 |
| JP | 3-118053 A | 5/1991 |
| JP | 2011-120782 A | 6/2011 |
| JP | 2015528713 A | 10/2015 |
| JP | 2018-114283 A | 7/2018 |
| WO | 03007198 A2 | 1/2003 |
| WO | 2005039417 A1 | 5/2005 |
| WO | 20090126953 A2 | 10/2009 |
| WO | 2012050634 A1 | 4/2012 |
| WO | 2013192598 A1 | 12/2013 |
| WO | 2014010760 A1 | 1/2014 |
| WO | 2015023665 A1 | 2/2015 |
| WO | 2015052718 A1 | 4/2015 |
| WO | 2015142762 A1 | 9/2015 |
| WO | 2016087539 A2 | 6/2016 |
| WO | 2016152255 A1 | 9/2016 |
| WO | 2017127202 A1 | 7/2017 |
| WO | 2017186799 A1 | 11/2017 |

OTHER PUBLICATIONS

Markelj et al.: "A review of 3D/2D registration methods for image-guided interventions", Medical Image Analysis, Oxford University Press, Oxford, GB, vol. 16, No. 3, pp. 642-661, Apr. 1, 2012.

Gong Ren Hui etal.: "Interactive initialization of 2D/3D rigid registration", Medical Physics, AIP, Melville, NY, US, vol. 40, No. 12, 14 pages, Dec. 2013.

Dumenil A et al.: "A versatile intensity-based 3D/2D rigid registration compatible with mobile C-arm for endovascular treatment of abdominal aortic aneurysm", International Journal of Computer Assisted Radiology and Surgery, Springer, DE, vol. 11, No. 9, pp. 1713-1729, May 26, 2016.

* cited by examiner

METHOD AND SYSTEM FOR IMPROVING 2D-3D REGISTRATION CONVERGENCE

CROSS REFERENCE TO RELATED APPLICATIONS

This application is a continuation-in-part of U.S. patent application Ser. No. 15/157,444 filed May 18, 2016, which is a continuation-in-part of U.S. patent application Ser. No. 15/095,883, filed Apr. 11, 2016, which is a continuation-in-part of U.S. patent application Ser. No. 14/062,707, filed on Oct. 24, 2013, which is a continuation-in-part application of U.S. patent application Ser. No. 13/924,505, filed on Jun. 21, 2013, which claims priority to provisional application No. 61/662,702 filed on Jun. 21, 2012 and claims priority to provisional application No. 61/800,527 filed on Mar. 15, 2013, all of which are incorporated by reference herein in their entireties for all purposes.

FIELD

The present disclosure relates to position recognition systems, and in particular, multi-image registration for robot assisted surgery.

BACKGROUND

In the field of image guidance, registration is the quantification of the transformation between two or more coordinate systems. After successful registration, the position of a tool or other object in one coordinate system, such as an optically tracked space, can be accurately displayed in another coordinate system, such as the medical image space. In the case where image guidance or robot-assisted image guidance is to be performed using a preoperative 3D image dataset such as a computed tomography (CT) scan or magnetic resonance imaging (MRI) scan, co-registration among multiple coordinate systems may be needed, such as between a preoperatively obtained anatomical CT or MRI coordinate system, an intraoperatively obtained anatomical coordinate system, a coordinate system of the tracking cameras, and the like.

One way to achieve co-registration of multiple coordinate systems is to use 2D-3D registration, such as where a pair of 2D x-ray radiographs of the patient is taken at the time of surgery, with the position of the x-ray machine and patient tracked using tracking cameras. The coordinate system in which the x-rays are taken may then be registered to a preoperatively obtained 3D medical image coordinate system through methods of 2D-3D registration. In this method, the 3D CT or MRI dataset may be used to generate 2D reconstructed planar images simulating x-ray radiographs. One way to generate 2D reconstructed simulated x-ray images from a 3D dataset is to trace and integrate the intensities along rays from a point source projected through the volumetric medical image on a 2D plane (e.g., a digitally reconstructed radiograph (DRR)). The DRRs are generated iteratively until they match the actual 2D x-ray images; that is, until the features or intensity characteristics of the bone structures on the DRRs and actual radiographs overlap within some tolerance. For instance, the iterative method could be a method such as Powell's Method, by which a cost function is minimized by starting with a guess and then adjusting parameters systematically until the error is within tolerance. As an example, the cost function could be constructed by subtracting the pixel intensities at locations within the images in the DRRs and the actual x-ray radiographs, and would be minimized when the pixel intensities agreed closest between X-ray and DRR in both views of the x-ray pair. Parameters of the cost function that could be adjusted between iterations may include the position and orientation of the 3D volumetric data, the x-ray source, angles of x-ray paths relative to the 3D volume, and the like, varied independently and/or simultaneously within the known (tracked) geometric constraint of the actual relative positions of the x-ray machine when the pair of shots were taken. Once a match is found, the position in the CT or MM coordinate system in which the x-ray machine must have been at the time the x-rays were taken is known from the parameters used in the calculation. Also, the position of the actual x-ray machine in the tracking coordinate system is known from tracking cameras. Therefore, the transformations between CT (or MRI), x-ray, and camera coordinate systems are determined.

Iterative methods as mentioned above, however, may be problematic because a large number of iterations may be required before a successful match is found. This may result in a long time delay, or worse, the iterations may fail to converge on a solution. Therefore, systems and methods are needed to improve the convergence of 2D-3D registration.

SUMMARY

The present disclosure provides methods and systems that improve 2D-3D registration convergence by initializing the computational configuration such that the simulated and actual x-rays agree fairly well before starting iterations. Improvements may result in less iteration, decrease processing time, lower incidence of failure to converge, and the like.

In one embodiment, there is provided a system and method for registration of digital medical images. The method includes the step of storing a 3D digital medical image having a 3D anatomical feature and a first coordinate system and storing a 2D digital medical image having a 2D anatomical feature and a second coordinate system. The method further includes the steps of storing a placement of a digital medical object on the 3D digital medical image and the 2D digital medical image and generating a simulated 2D digital medical image from the 3D digital medical image, wherein the simulated 2D digital medical image comprises a simulated 2D anatomical feature corresponding to the 3D anatomical feature. The 2D anatomical feature is compared with the simulated 2D anatomical feature until a match is reached and a registration of the first coordinate system with the second coordinate system based on the match is determined.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE FIGURES

The invention and the following detailed description of certain embodiments thereof may be understood by reference to the following figures.

Figure 1:
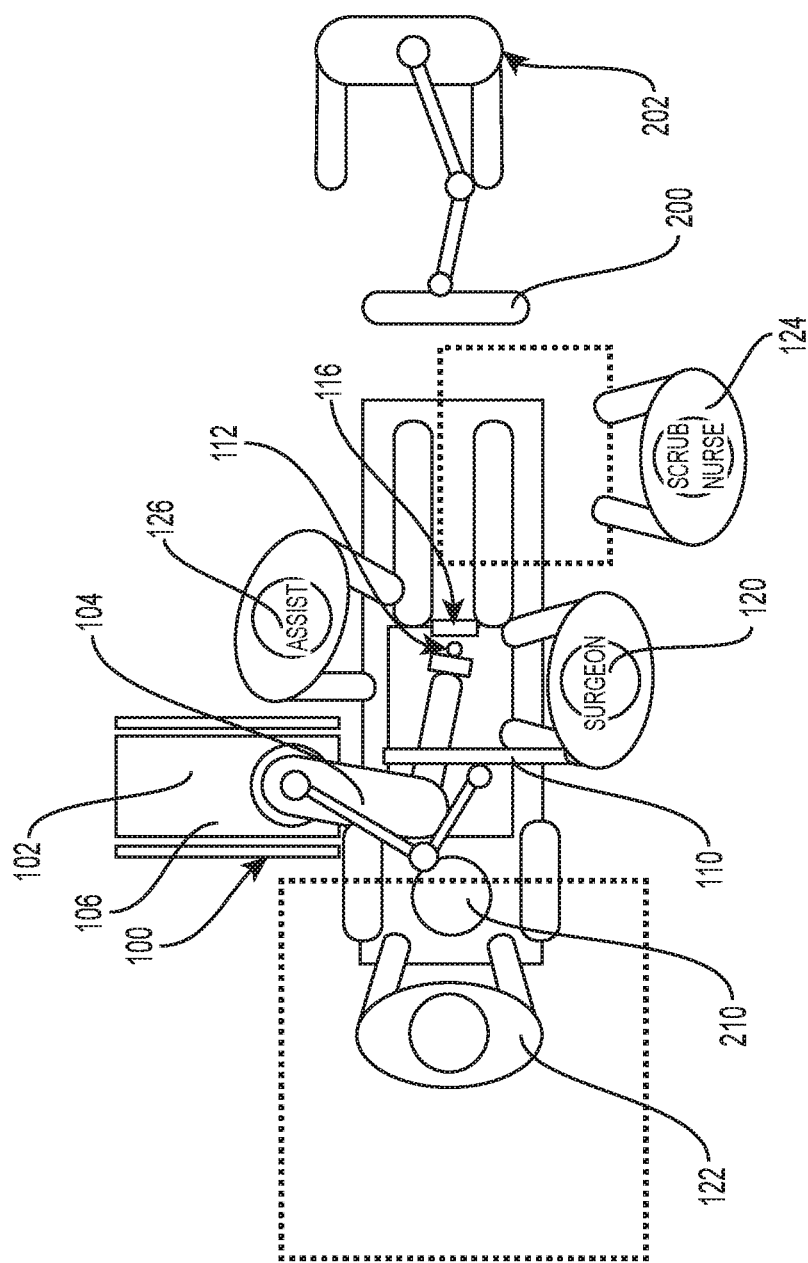
FIG. 1 is an overhead view of a potential arrangement for locations of the robotic system, patient, surgeon, and other medical personnel during a surgical procedure.

While the invention has been described in connection with certain preferred embodiments, other embodiments would be understood by one of ordinary skill in the art and are encompassed herein.

DETAILED DESCRIPTION

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
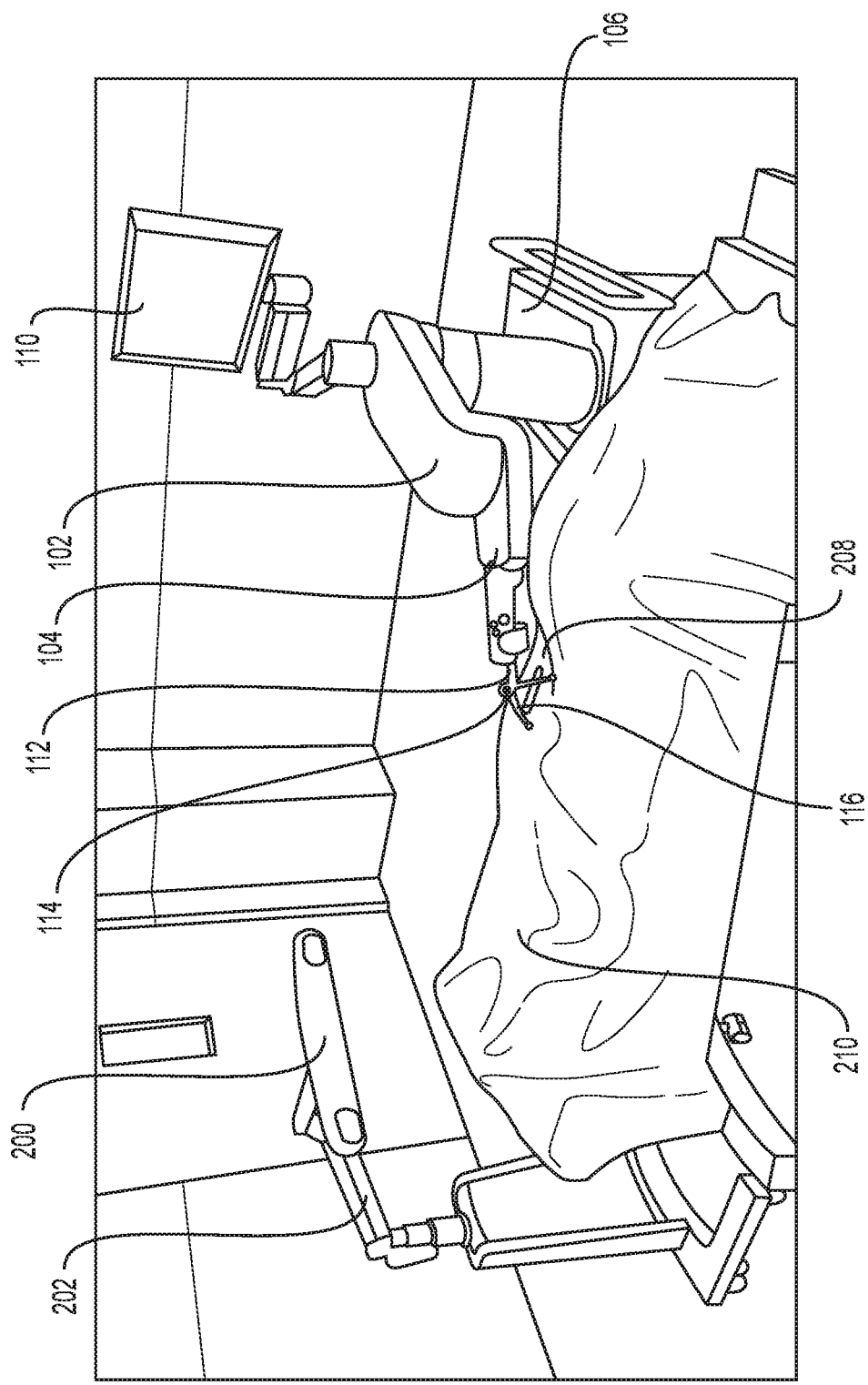
FIG. 2 illustrates the robotic system including positioning of the surgical robot and the camera relative to the patient according to one embodiment.

Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end effector 112, for example, including a guide tube 114, and one or more tracking markers 118. The surgical robot system 100 may include a patient tracking device 116 also including one or more tracking markers 118, which is adapted to be secured directly to the patient 210 (e.g., to the bone of the patient 210). The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end effector 112 and the display 110. A surgical assistant 126 may be positioned across from the surgeon 120 again with access to both the end effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End effector 112 may be coupled to the robot arm 104 and controlled by at least one motor. In exemplary embodiments, end effector 112 can comprise a guide tube 114, which is able to receive and orient a surgical instrument 608 (described further herein) used to perform surgery on the patient 210. As used herein, the term "end effector" is used interchangeably with the terms "end-effectuator" and "effectuator element." Although generally shown with a guide tube 114, it will be appreciated that the end effector 112 may be replaced with any suitable instrumentation suitable for use in surgery. In some embodiments, end effector 112 can comprise any known structure for effecting the movement of the surgical instrument 608 in a desired manner.

The surgical robot 102 is able to control the translation and orientation of the end effector 112. The robot 102 is able to move end effector 112 along x-, y-, and z-axes, for example. The end effector 112 can be configured for selective rotation about one or more of the x-, y-, and z-axis, and a Z Frame axis (such that one or more of the Euler Angles (e.g., roll, pitch, and/or yaw) associated with end effector 112 can be selectively controlled). In some exemplary embodiments, selective control of the translation and orientation of end effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end effector 112 and/or the surgical instrument 608. Thus, in use, in exemplary embodiments, a physician or other user can operate the system 100, and has the option to stop, modify, or manually control the autonomous movement of end effector 112 and/or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, or on the end effector 112. In exemplary embodiments, at least one tracking marker 118 of the plurality of tracking markers 118 can be mounted or otherwise secured to the end effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screw driver, dilator, implant inserter, or the like). Thus, the tracking markers 118 enable each of the marked objects (e.g., the end effector 112, the patient 210, and the surgical tools 608) to be tracked by the robot 102. In exemplary embodiments, system 100 can use tracking information collected from each of the marked objects to calculate the orientation and location, for example, of the end effector 112, the surgical instrument 608 (e.g., positioned in the tube 114 of the end effector 112), and the relative position of the patient 210.

In exemplary embodiments, one or more of markers 118 may be optical markers. In some embodiments, the positioning of one or more tracking markers 118 on end effector 112 can maximize the accuracy of the positional measurements by serving to check or verify the position of end effector 112. Further details of surgical robot system 100 including the control, movement and tracking of surgical robot 102 and of a surgical instrument 608 can be found in co-pending U.S. patent application Ser. No. 13/924,505, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
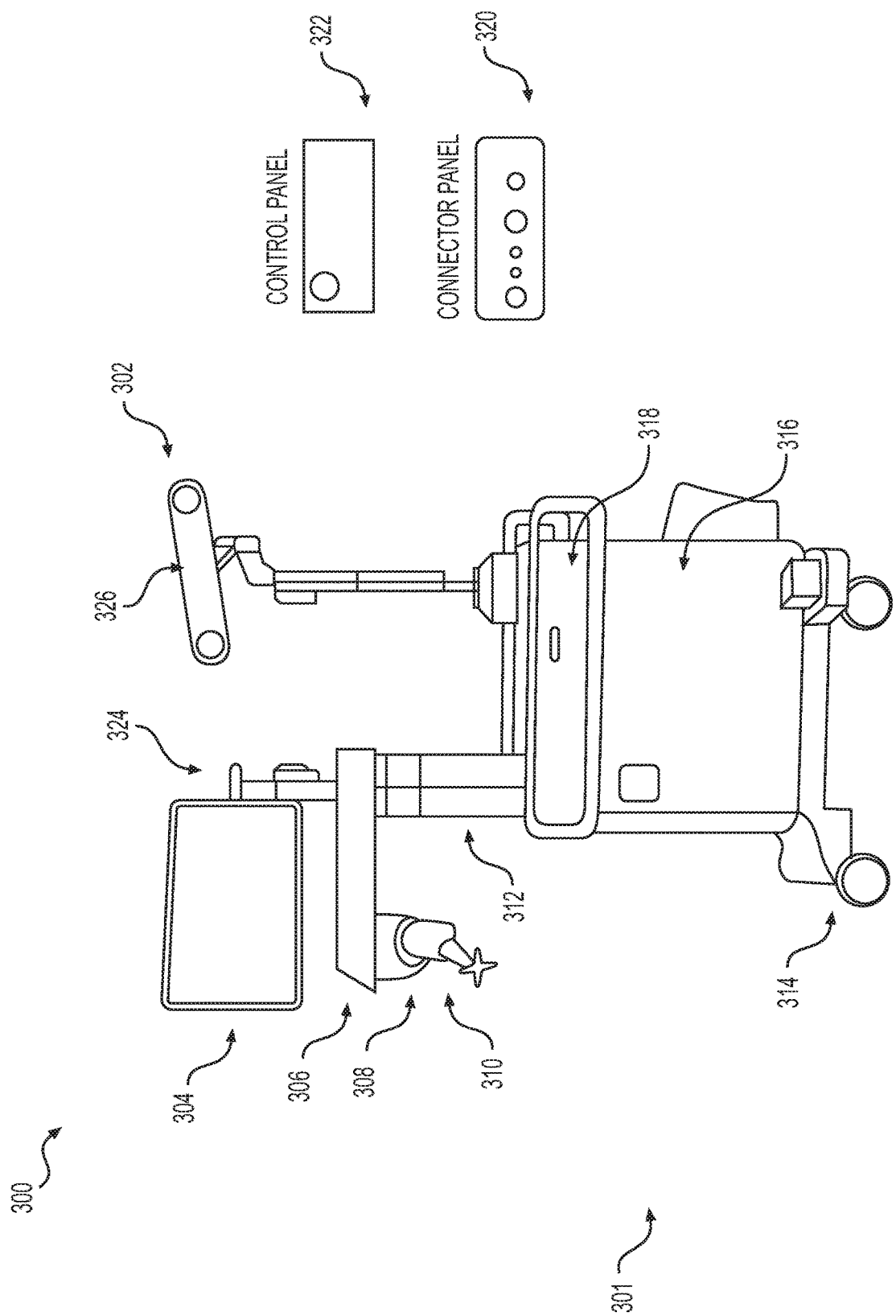
FIG. 3 illustrates a surgical robotic system in accordance with an exemplary embodiment.
Figure 4:
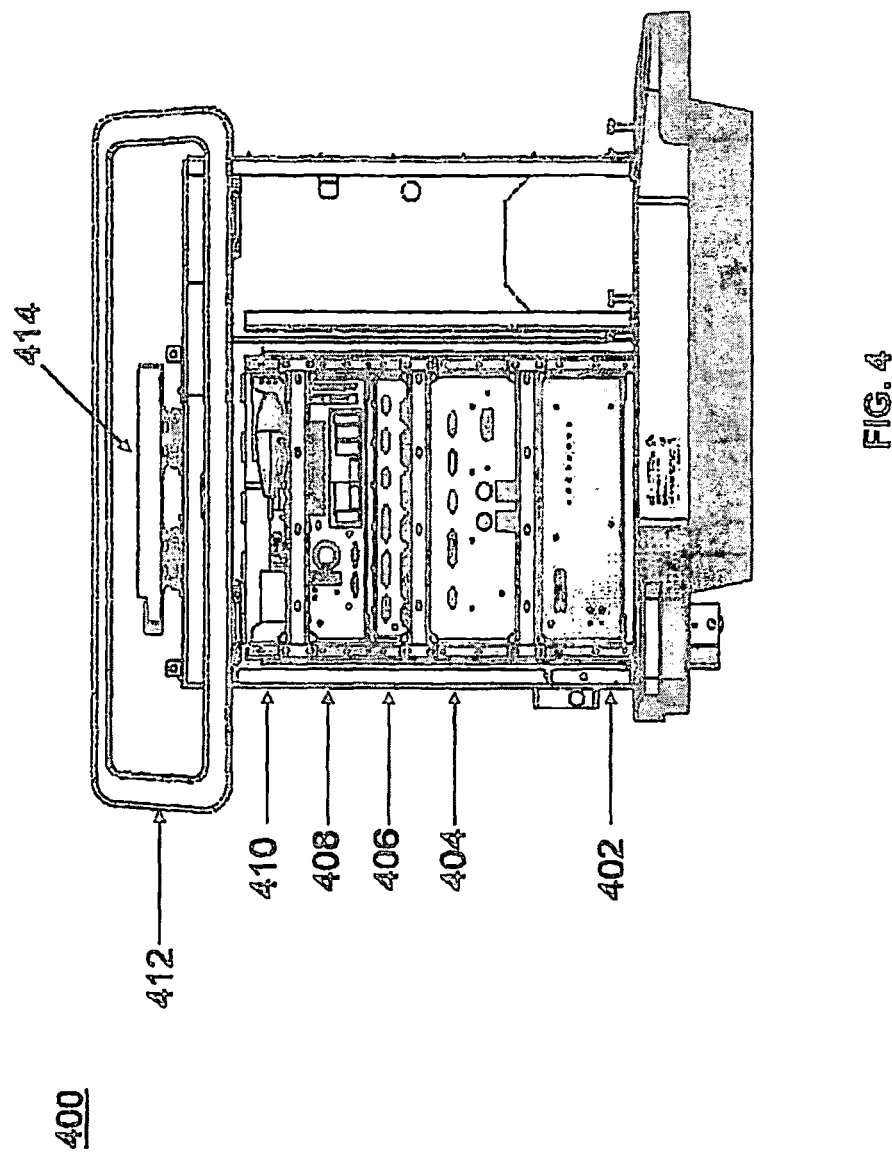
FIG. 4 illustrates a portion of a surgical robot in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2. FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
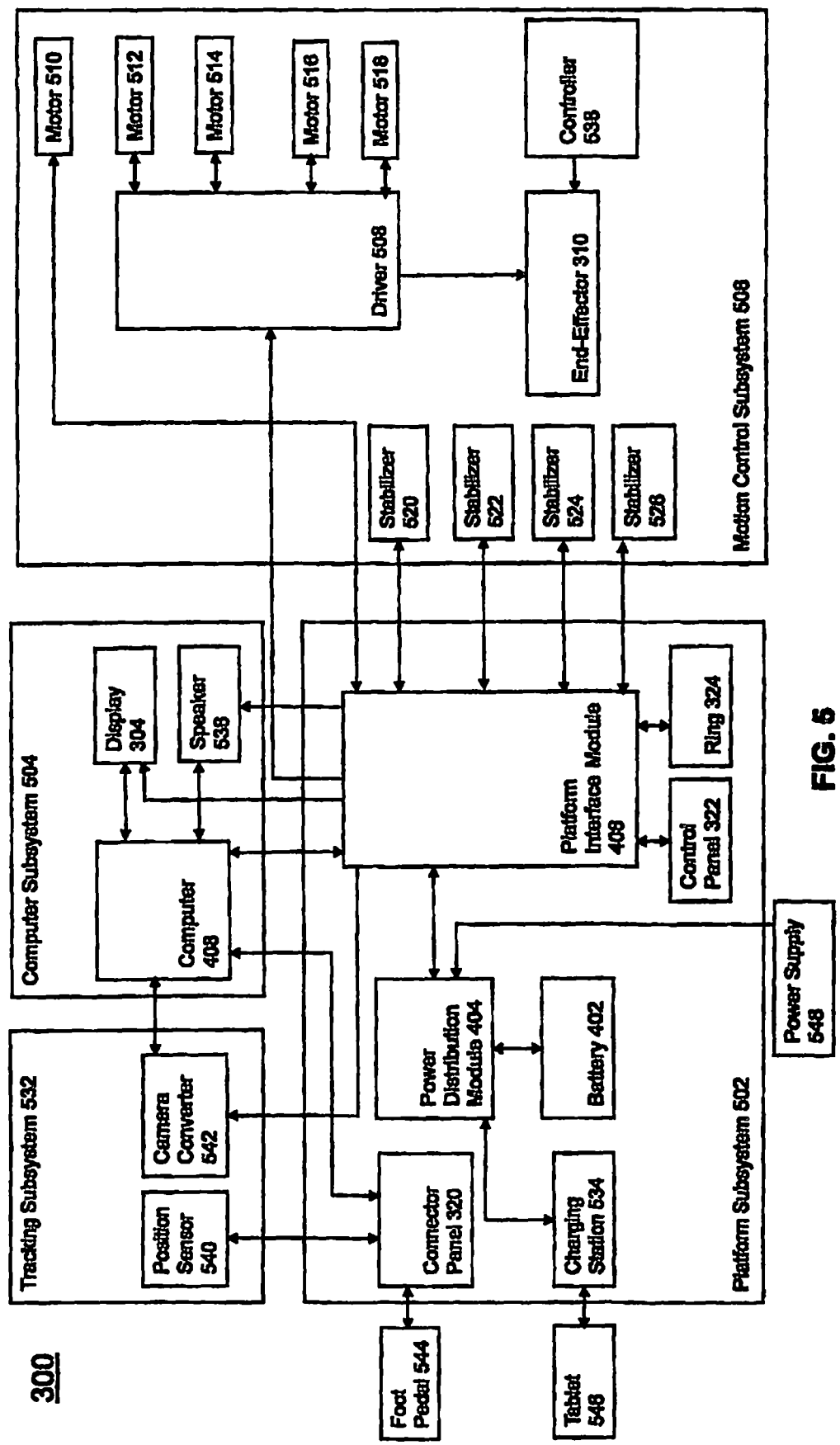
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein. Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure. Motion control subsystem 506 may be configured to physically move vertical column 312, upper arm 306, lower arm 308, or rotate end effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end effector 310 in a manner such that one may control the roll and one may control the tilt, thereby providing multiple angles that end effector 310 may be moved. These movements may be achieved by controller 538 which may control these movements through load cells disposed on end effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on three dimensional image of the patient's anatomy on display 304. The user may initiate this automatic movement by stepping on foot pedal 544 or some other input means.

Figure 6:
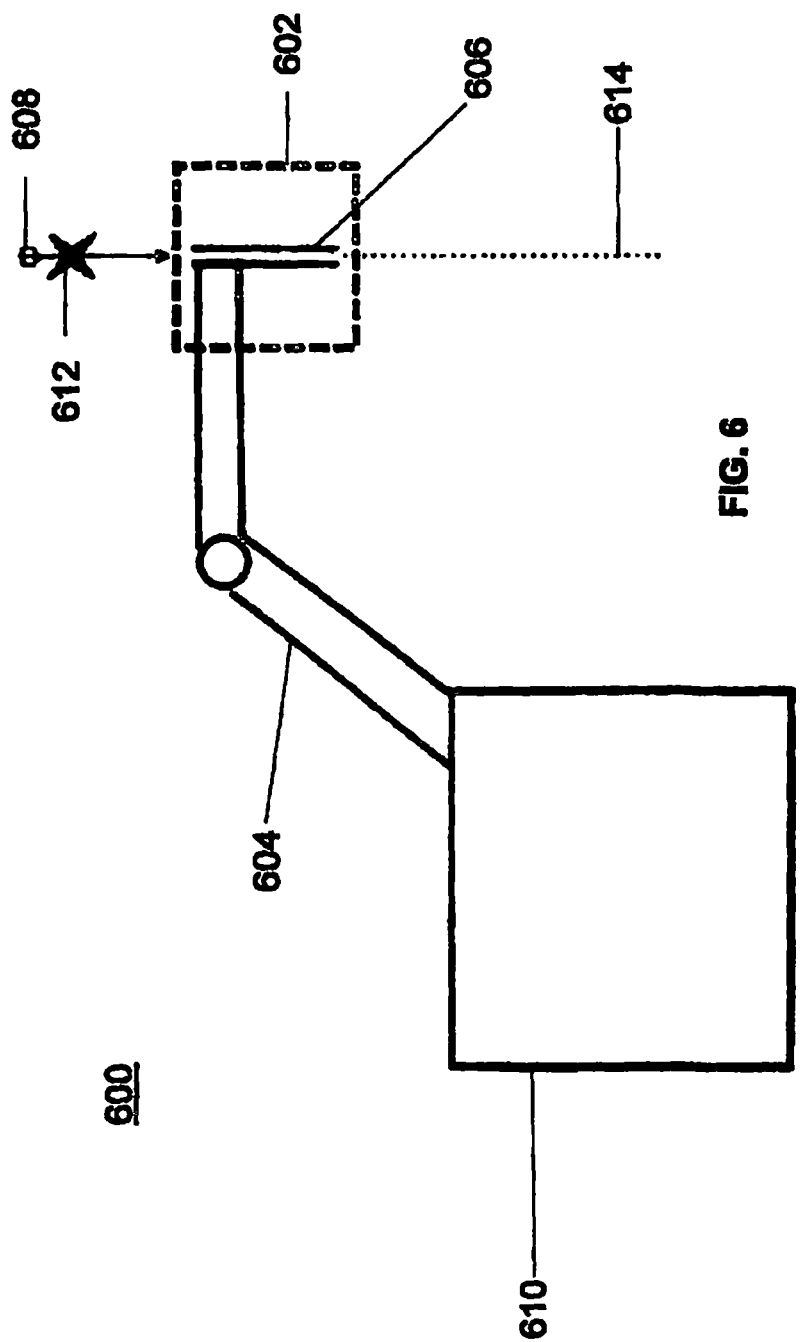
FIG. 6 illustrates a surgical robot in accordance with an exemplary embodiment.

FIG. 6 illustrates a surgical robot system 600 consistent with an exemplary embodiment. Surgical robot system 600 may comprise end effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end effector 602 so that surgical robot system 600 may assist a user (for example, a surgeon) in operating on the patient 210. Surgical robot system 600 may be consistent with previously described surgical robot system 100 and 300.

Figure 8:
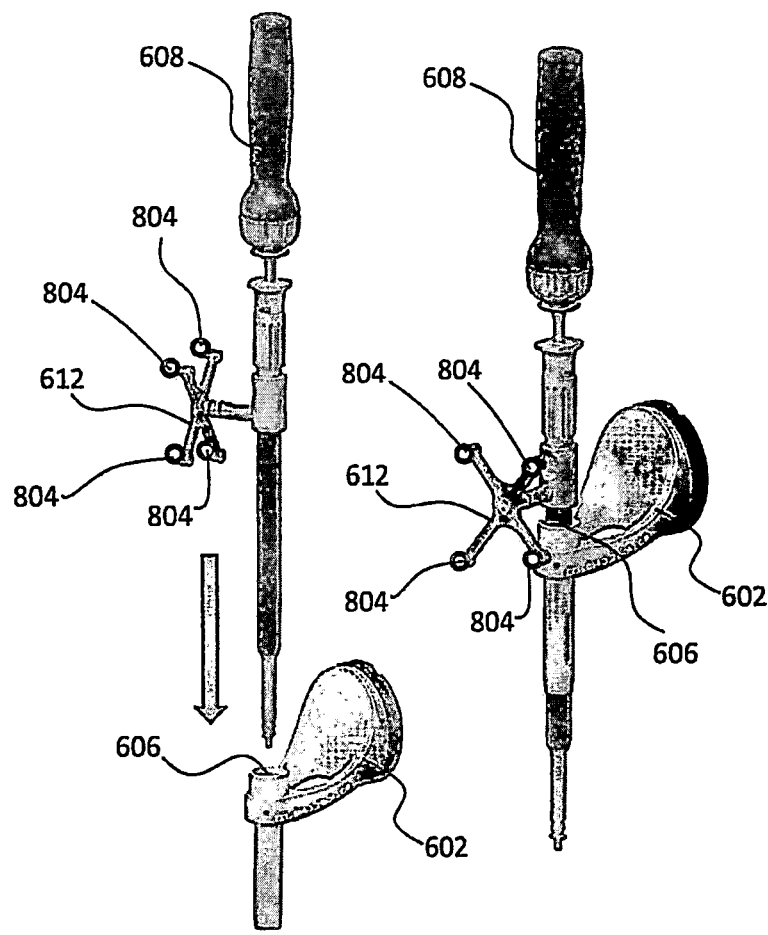
FIG. 8 illustrates a surgical instrument and the end effector, before and after, inserting the surgical instrument into the guide tube of the end effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end effector 602, and/or the patient 210. The tracking devices may be consistent with those structures described in connection with camera stand 302 and tracking subsystem 532.

Figure 7A:
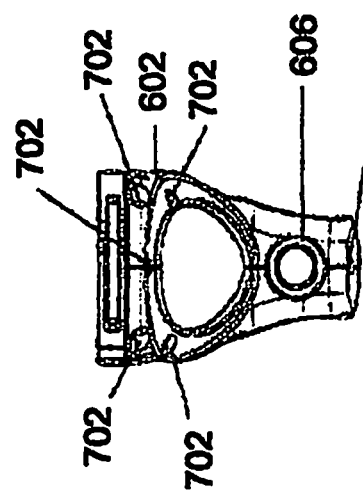
FIGS. 7A-7C illustrate an end effector in accordance with an exemplary embodiment.
Figure 7B:
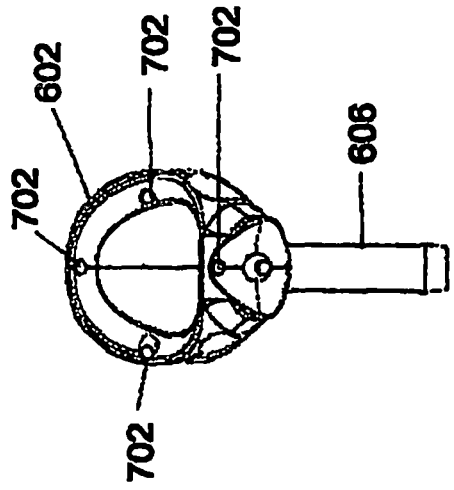
Figure 7C:
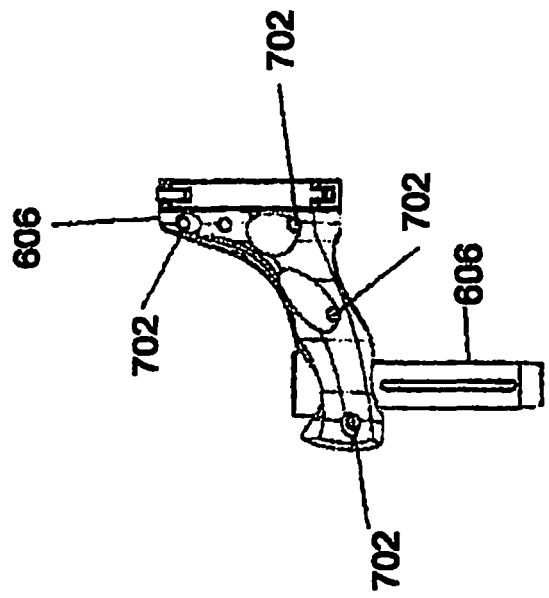

FIGS. 7A, 7B, and 7C illustrate a top view, front view, and side view, respectively, of end effector 602 consistent with an exemplary embodiment. End effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end effector 602 may be controlled by the system 100, 300, 600, and when the markers 702 are deactivated, the end effector 602 may be locked in position and unable to be moved by the system 100, 300, 600.

Markers 702 may be disposed on or within end effector 602 in a manner such that the markers 702 are visible by one or more cameras 200, 326 or other tracking devices associated with the surgical robot system 100, 300, 600. The camera 200, 326 or other tracking devices may track end effector 602 as it moves to different positions and viewing angles by following the movement of tracking markers 702. The location of markers 702 and/or end effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end effector 602 is in a desirable position in relation to robot arm 604, robot base 610, the patient 210, and/or the user.

For example, as shown in FIG. 7A, markers 702 may be placed around the surface of end effector 602 so that a tracking device placed away from the surgical field 208 and facing toward the robot 102, 301 and the camera 200, 326 is able to view at least 3 of the markers 702 through a range of common orientations of the end effector 602 relative to the tracking device 100, 300, 600. For example, distribution of markers 702 in this way allows end effector 602 to be monitored by the tracking devices when end effector 602 is translated and rotated in the surgical field 208.

In addition, in exemplary embodiments, end effector 602 may be equipped with infrared (IR) receivers that can detect when an external camera 200, 326 is getting ready to read markers 702. Upon this detection, end effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end effector 602 and adjust the instrument 608 is evident in FIG. 8. The hollow tube or guide tube 114, 606 of the end effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screw driver is exemplified as the surgical tool 608, it will be appreciated that any suitable surgical tool 608 may be positioned by the end effector 602. By way of example, the surgical instrument 608 may include one or more of a guide wire, cannula, a retractor, a drill, a reamer, a screw driver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figure 9:
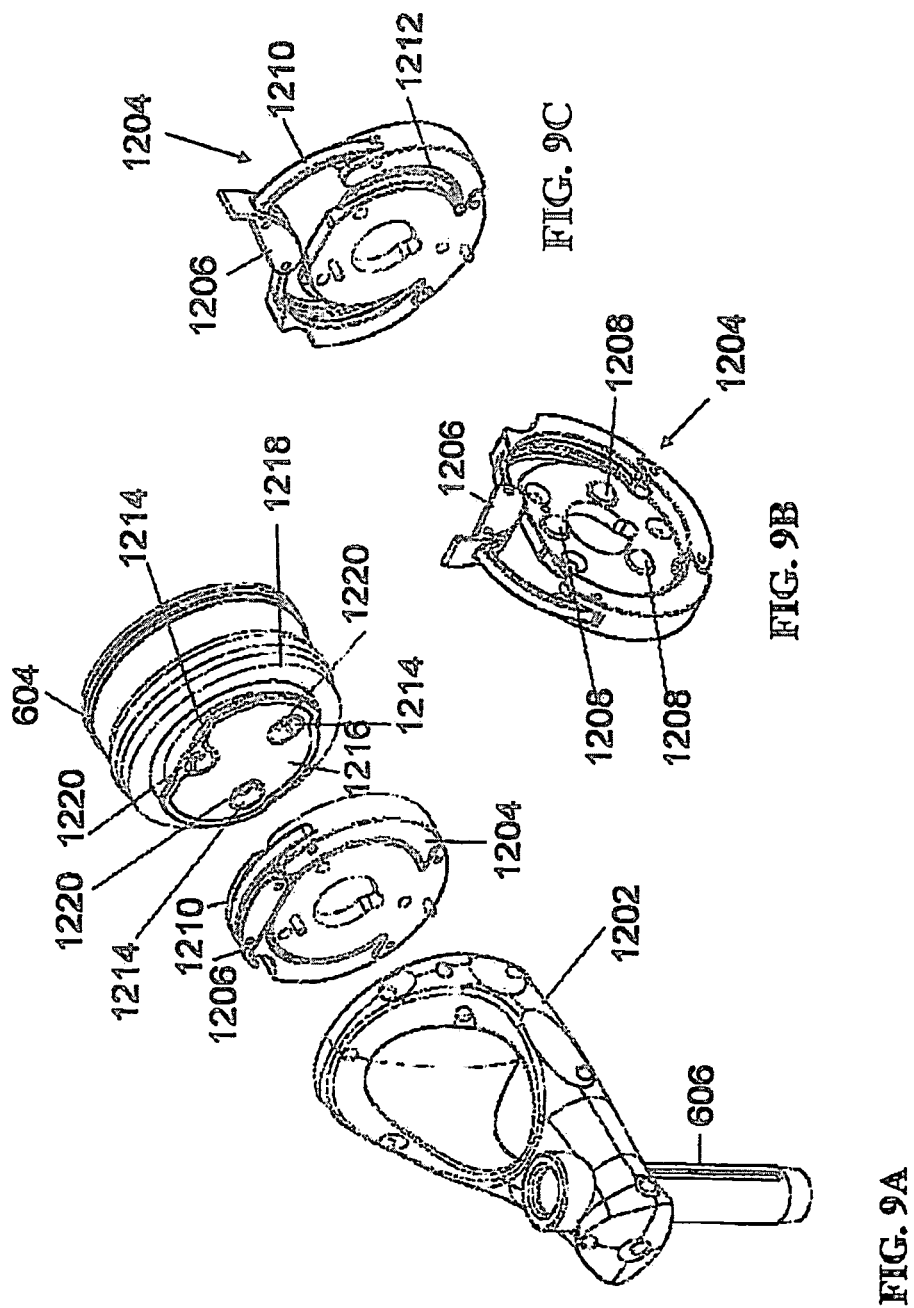
FIGS. 9A-9C illustrate portions of an end effector and robot arm in accordance with an exemplary embodiment.

FIGS. 9A-9C illustrate end effector 602 and a portion of robot arm 604 consistent with an exemplary embodiment. End effector 602 may further comprise body 1202 and clamp

1204. Clamp 1204 may comprise handle 1206, balls 1208, spring 1210, and lip 1212. Robot arm 604 may further comprise depressions 1214, mounting plate 1216, lip 1218, and magnets 1220. End effector 602 may mechanically interface and/or engage with the surgical robot system and robot arm 604 through one or more couplings. For example, end effector 602 may engage with robot arm 604 through a locating coupling and/or a reinforcing coupling. Through these couplings, end effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end effector 602 regardless of the orientation of end effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end effector 602 to robot arm 604 as lip 1212 and lip 1218 engage clamp 1204 in a manner to secure end effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end effector 602 may be robustly secured to robot arm 604.

Spring 1210 may be a curved beam in tension. Spring 1210 may be comprised of a material that exhibits high stiffness and high yield strain such as virgin PEEK (polyether-ether-ketone). The linkage between end effector 602 and robot arm 604 may provide for a sterile barrier between end effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end effector 602 and/or robot arm 604 that slips over an interface between end effector 602 and robot arm 604 and tightens with a screw mechanism, an over center linkage, or a cam mechanism.

Figure 10:
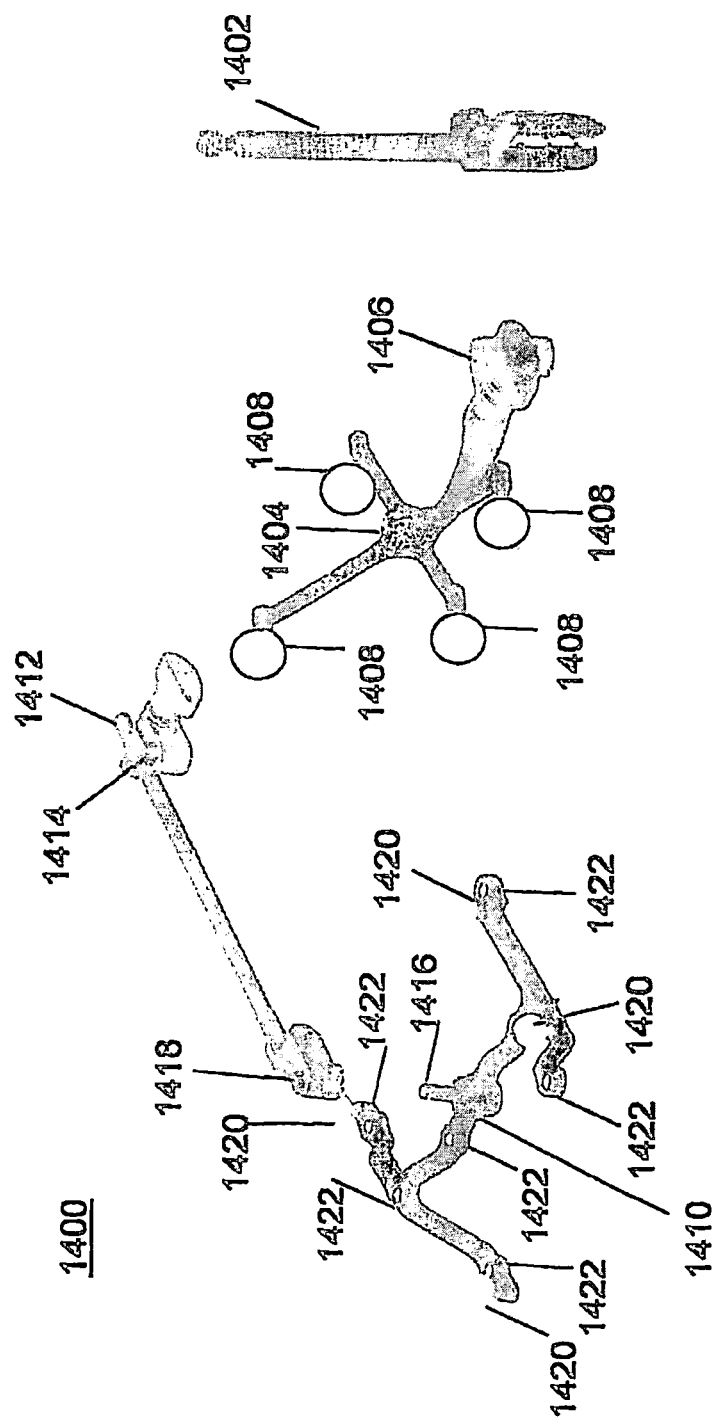
FIG. 10 illustrates a dynamic reference array, an imaging array, and other components in accordance with an exemplary embodiment.
Figure 11:
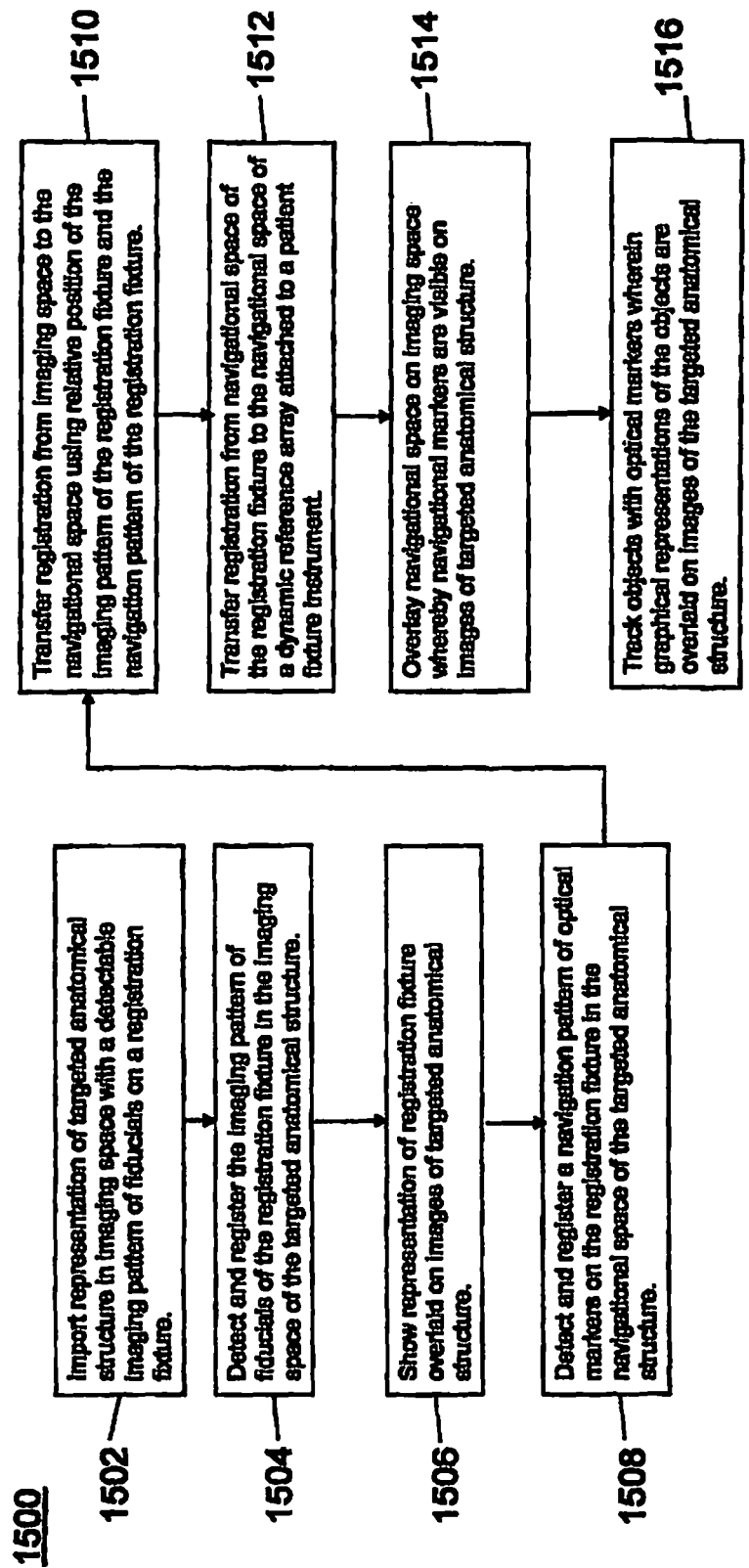
FIG. 11 illustrates a method of registration in accordance with an exemplary embodiment.

Referring to FIGS. 10 and 11, prior to or during a surgical procedure, certain registration procedures may be conducted in order to track objects and a target anatomical structure of the patient 210 both in a navigation space and an image space. In order to conduct such registration, a registration system 1400 may be used as illustrated in FIG. 10.

In order to track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
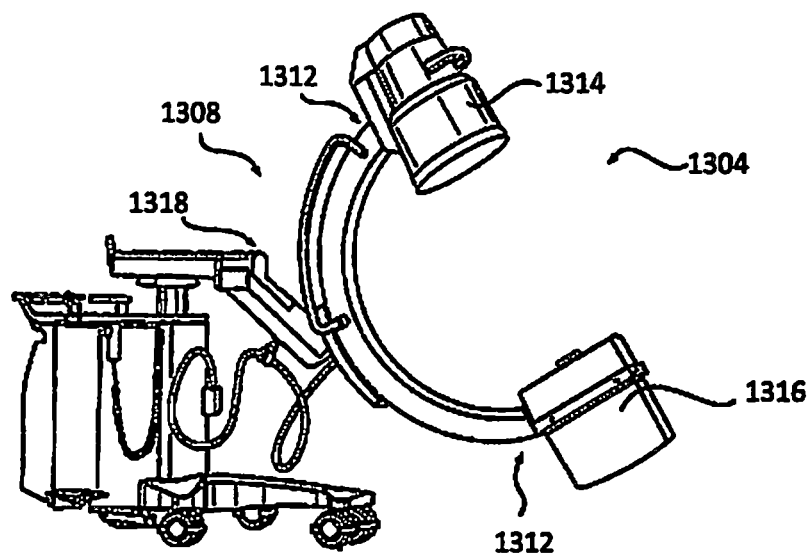
FIG. 12A-12B illustrate embodiments of imaging devices according to exemplary embodiments.
Figure 12B:
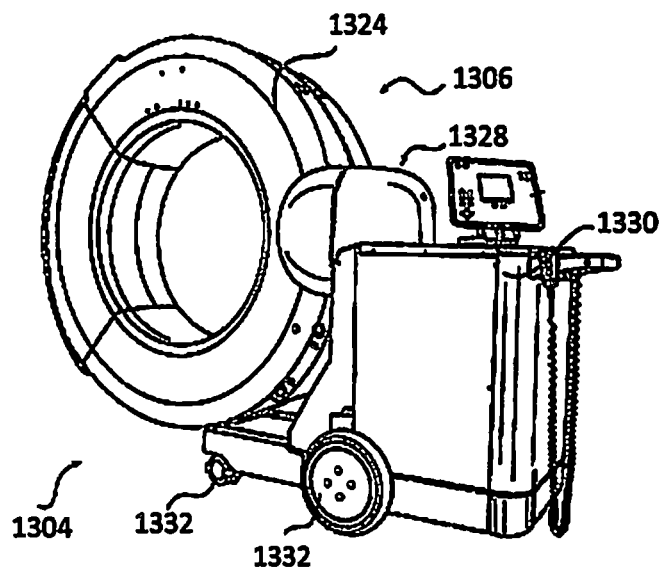

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes.

Although certain imaging systems 1304 are exemplified herein, it will be appreciated that any suitable imaging system may be selected by one of ordinary skill in the art.

Robot system 300 may include an image registration facility, for example as part of computer subsystem 504 and further, for example, as part of computer 406. Registration facility may be specifically configured to perform registration by acquiring and processing patient medical images in preparation for a medical procedure (e.g., surgery). The registration may be conducted in order to position a medical object in one coordinate system relative to another coordinate system, such as between pre-operative, intra-operative, and real-time image data of a patient 210. A medical object may be a passive implant (e.g., screw, pin), electronics-based implant (e.g., artificial pacemaker, cochlear implant), bioactive implant (e.g., pharmaceutical implant), biological transplant tissue, artificial transplant material, and the like. For instance, image guidance or robot-assisted image guidance may be performed using a preoperative 3D image dataset such as a computed tomography (CT) scan or magnetic resonance imaging (MRI) scan. Co-registration of multiple coordinate systems may then be needed, such as between the preoperatively obtained anatomical CT or MM coordinate system, an intraoperatively obtained anatomical coordinate system, a coordinate system of the tracking cameras, and the like. Co-registration of multiple coordinate systems may utilize 2D-3D registration, such as where multiple 2D x-ray radiographs of the patient are taken at the time of surgery, where the position of the x-ray machine and the patient are tracked (e.g., using tracking cameras). The coordinate system in which the x-rays were taken may then be registered to the preoperatively obtained 3D medical image coordinate system through 2D-3D registration.

Co-registration of multiple coordinate systems may involve an iterative process. For example, a 3D CT or MM dataset may be used to generate 2D reconstructed planar images simulating x-ray radiographs. The generation of 2D reconstructed simulated x-ray images from a 3D dataset may comprise tracing and integrating the intensities along rays from a point source projected through the volumetric medical image on a 2D plane, such as in preparation for generating a digitally reconstructed radiograph (DRR). DRRs may then be generated iteratively until they match the actual 2D x-ray images; that is, until the features or intensity characteristics of the bone structures on the DRRs and actual radiographs overlap within some tolerance. In embodiments, initial conditions for the computational configuration may be established in order to reduce the number of iterations required in this process. For instance, a computational configuration may be initialized such that simulated and actual x-rays agree to a predetermined level before starting iterations, thus potentially reducing the number of iterations and likelihood for reaching co-registration convergence associated with registration of the multiple coordinate systems.

Figure 13:
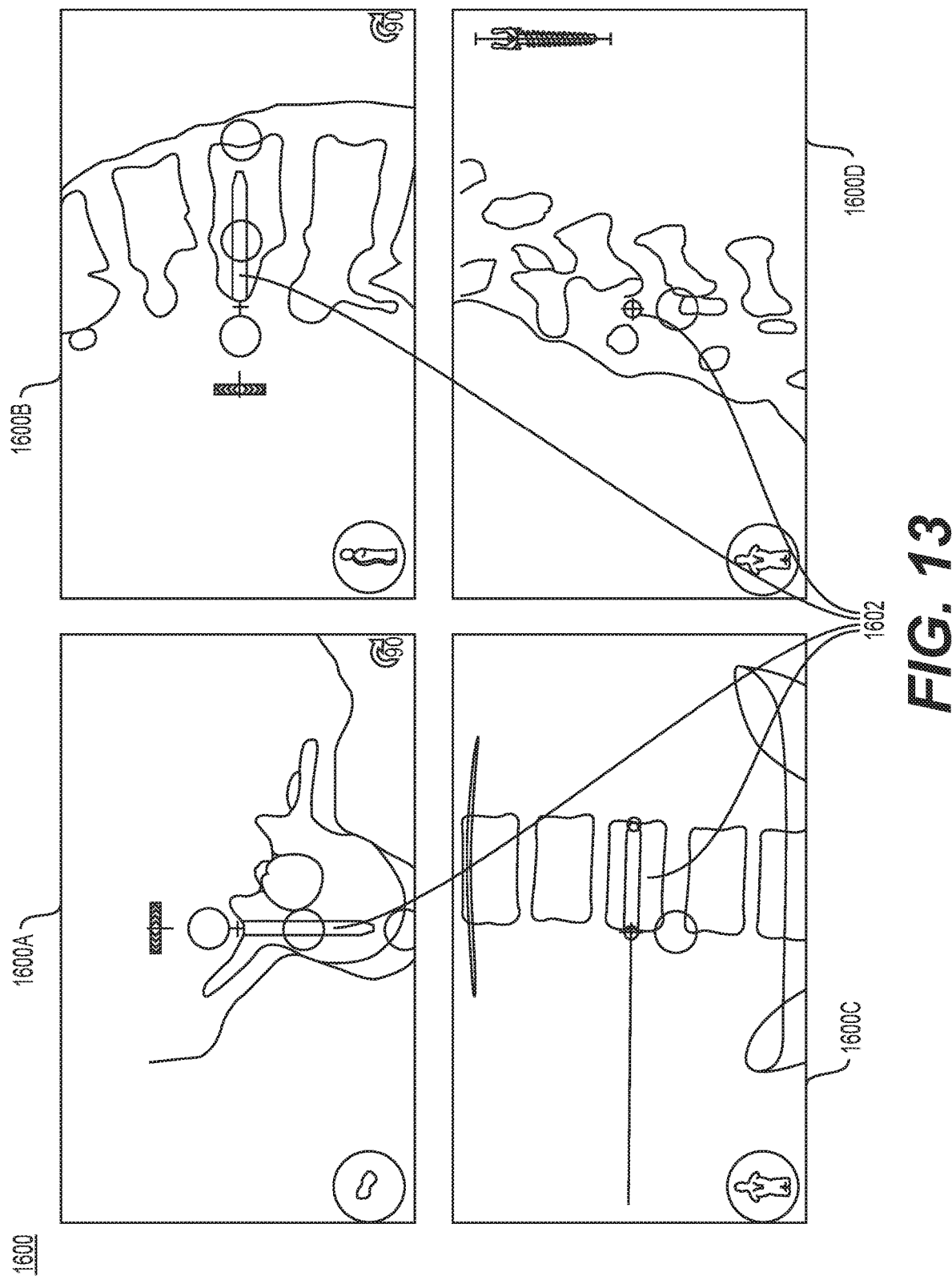
FIG. 13 illustrates a process of planning the trajectory of a pedicle screw on a single lumbar vertebra in multiple slices through a computed tomography volume.
Figure 14:
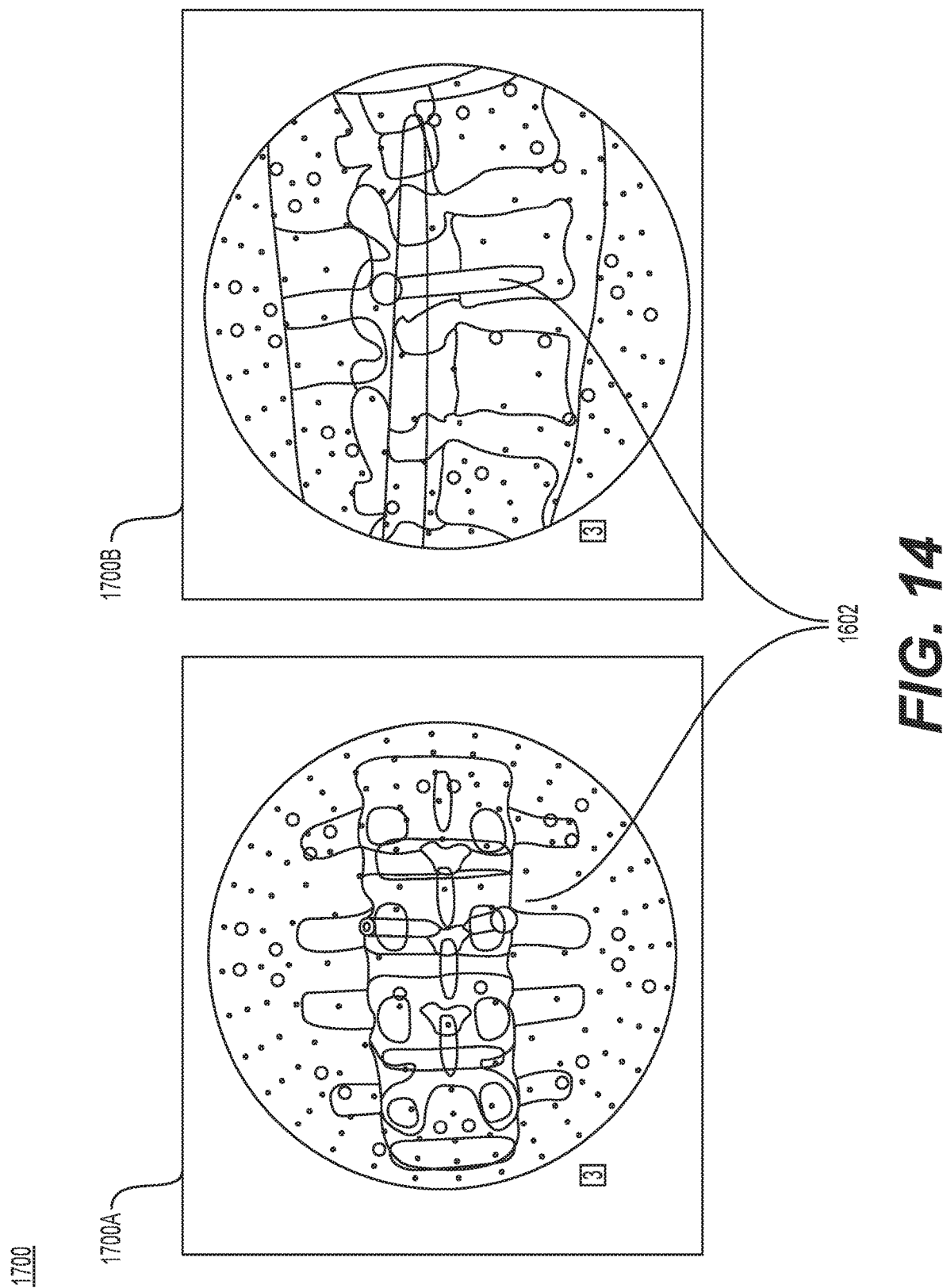
FIG. 14 illustrates a process of planning the trajectory of a pedicle screw on a single lumbar vertebra from multiple views on an x-ray.

Initial conditions for the computational configuration for registration of multiple coordinate systems may include a step where a user (e.g., surgeon, doctor, medical technician, medical assistant, and the like), manipulates software to enable graphic objects representing surgical objects that he/she intends to implant during a surgical procedure to be superimposed over the anatomy that appears on multiple intraoperatively obtained images (e.g., x-ray images). In embodiments, when the graphic objects are applied, their appearance may be depicted as similar to the appearance of shadows that would appear on x-ray if the surgical hardware had been implanted and an x-ray then taken. Before or after placing the graphic objects on 2D images, the user may also manipulate software such that graphic objects are superimposed on 3D medical images in the same anatomical location as the graphic objects applied to the 2D images. In an example, preoperative 3D medical images may be used together with intraoperative 2D x-ray radiographs, where the user would likely first (preoperatively) plan screw placement on the 3D medical images, then intraoperatively plan the same screws on two or more 2D x-ray radiographs. For instance, before surgery, the user could use the system to plan a pedicle screw at a particular vertebra on 3D preoperative CT or MRI images and then plan the same pedicle screw on x-rays by interacting with the system in the operating room before beginning surgery. FIG. 13 shows part of the process of planning the trajectory of a pedicle screw 1602 on a single lumbar vertebra (L3) from mutually orthogonal slices through a computed tomography volume 1600 (top left quadrant 1600A, top right quadrant 1600B, and bottom right quadrant 1600D) and, optionally, a 3D posterior perspective view (bottom left quadrant 1600C). To plan the screw trajectory, the user manipulates the positions of graphic object representing the screw 1602 that is overlaid on the computed tomography volume image volume 1600 through interaction with the system (e.g., through mouse, touchscreen, voice command, or other interactive methods). FIG. 14 shows part of the process of planning the trajectory of the pedicle screw 1602 on a single lumbar vertebra (L3) on x-ray views 1700 from an anteroposterior x-ray view 1700A and a lateral x-ray view 1700B. To plan the screw trajectory, the user manipulates the positions of graphic object representing screw 1602 that is overlaid on the x-ray images through interaction with the system.

As the user may not be able to exactly match the locations of the hardware in the 2D and 3D image sets the user may be enabled to make placement within a tolerance range (e.g., within set linear or rational dimensional limits), within predetermined placement criteria (e.g., placement constraints stored in a profile for different surgical objects, anatomical features, and the like). The system may then use the object locations in different coordinate systems (e.g., both the CT (or MM) and x-ray coordinate systems) to determine areas of interest on the images so that the iterative process starts on and focuses within this region in attempting to match simulated and actual images.

In embodiments, the system could use as little as one object planned in 2D and 3D. However, using two or more planned objects may result in an improved performance since one planned object provides limited degrees of freedom (e.g., 5 of 6 degrees of freedom). That is, with one planned object, it may not be clear what the orientation of the anatomy is in its rotational alignment of the object, such as around the shaft of a surgical screw. Using the entirety of the intended construct (e.g., multiple object placements) has the additional benefit of demarking the entire region of interest, whereas if only a portion of the surgical hardware construct is used, the algorithm may need to extrapolate outside of the indicated region to match anatomical features (e.g., bones) that may or may not need to be accurately targeted.

It may not be immediately clear to the user who has already planned the placement of objects using 3D medical images on CT or MM where the corresponding objects should go when planning on 2D planar x-ray radiographs. The reason for the difficulty in correlating the images is that the 3D medical image planning occurs while the user is looking at two or three mutually orthogonal slices through the image volume; that is, only the anatomy on the slice itself may be shown, not anatomy in front of or behind that slice. However, when planning in 2D, the user may be looking at two or more projections through the same anatomical features. Additionally, by the nature of x-rays, the projected images originate from a point source and travel through the patient to an image intensifier or collector plate through a conical beam, introducing parallax that may be difficult to reconcile mentally by the user when comparing 2D and 3D images. If the 3D medical image is already present at the time the 2D images are shot, as it would be if a preoperative CT or MRI is used, DRRs such as those that are generated in a matching algorithm may be used as a tool for the user when planning object placement on 2D images. That is, the software may be able to generate and display DRRs that the user can quickly adjust to be roughly similar in appearance to the actual x-ray radiographs (e.g., a default may be anteroposterior and lateral x-rays) where software can automatically superimpose the objects that were planned on 3D images onto these DRRs. Given this procedure it may be relatively easy for the user to plan object placement that is similarly placed on the actual 2D x-ray radiographs when side by side with the objects visible on DRRs.

Providing for initial conditions as part of registration may help an iterative matching algorithm to converge more quickly because the approximate location of object placement is known to the system, such as in both the 2D and 3D images. Although the object positions may not agree exactly because of user placement error, if placed within the constraints set by the system (or by the user through placement constraints stored in a profile) may be close enough that the algorithm can start making small instead of coarse adjustments to converge to a solution. In the alternative circumstance, where no starting position is provided, the algorithm may start varying the orientation of the simulated x-rays in the wrong direction, potentially converging on a minimum error value that exceeds tolerance (e.g., where convergence is not reached).

Another advantage of providing an initial placement on the images is that the user is able to place objects on actual imaged anatomy rather than with reference to identification of landmarks on the anatomy. Identification of landmarks on the anatomy can be challenging for medical personnel because it may be difficult to visualize, such as to which way bony curvatures travel, especially in 2D views. For example, if the user is asked to mark the outermost extension of a bony process but the bony process is oriented toward the direction of the x-ray path, it may be unclear what portion of the resulting shadow corresponds to the outermost extension of the process. However, most users of the process should be familiar with the appearance of surgical objects when optimally placed on both 2D and 3D views, and should therefore already be familiar with how the objects should appear on medical images.

Initial placement may also automatically fulfill the purpose of segmentation sometimes required by algorithms for matching 2D to 3D medical images, such as where the user must superimpose ranges (e.g., boxes) around each anatomical feature (e.g., vertebra) on 2D or 3D images, thereby indicating to the software the anatomical level of each vertebra so that the matching algorithm can be performed independently for each spinal level. The reason for independently registering each anatomical feature is that the 3D image is generally taken while the patient is lying supine and the 2D images are generally taken while the patient is lying prone, and even if the images were taken in roughly the same orientation, there could be some movement between the features, which would mean that 2D-3D registration at one level would not necessarily be valid at another level. By setting initial conditions through placement of objects prior to the registration process (e.g., iterative convergence of multiple coordinate systems), the user knows the level where an object is being planned. For example, if a surgeon intends to perform a long construct from LI to LS, he or she may plan screws in all of these levels preoperatively on a 3D image, then again intraoperatively on a 2D image. By performing these planning steps, the software would be provided similar information about the anatomical level of each part of the image. For instance, an image analysis algorithm may then check for a shift in the pixel intensity of the image while moving outward away from the objects that could be used to automatically segment the edges of each level on 3D and 2D images. Additionally, the known general shape of anatomical features (e.g., vertebra) and the known general spacing between adjacent objects (e.g., surgical screws) can be used to improve an automatic algorithm for detecting edges of the anatomical feature and the object. With reference to the preceding example, the software may then independently run the matching algorithm on each vertebra from LI to LS to give unique registration for each level.

Wherein the present disclosure utilizes surgical examples such as insertion of surgical screws into a spinal column (e.g., as depicted in FIGS. 13 and 14), the present disclosure presents methods and systems for improving the registration convergence of multiple anatomic images utilized in any medical procedure for which medical objects are implanted into a body. One skilled in the art will appreciate that the methods and system disclosed herein may be applied to any medical implant or transplant known in the art.

Figure 15:
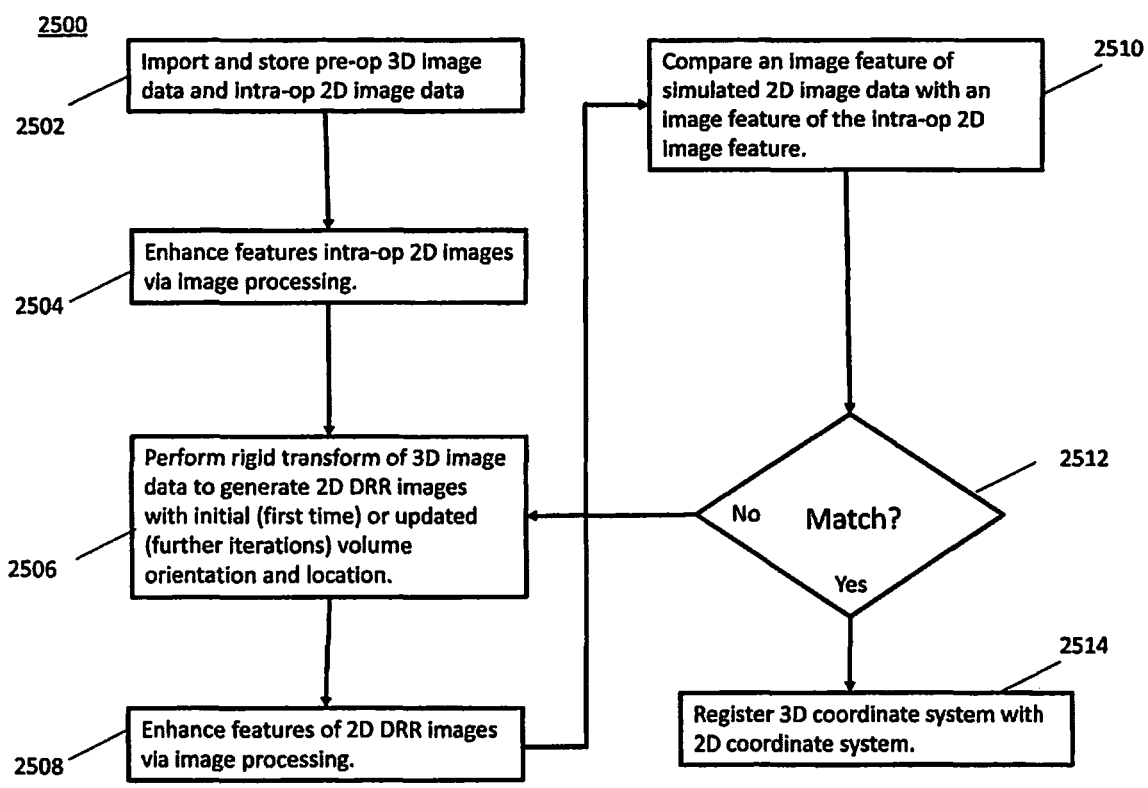
FIG. 15 illustrates an exemplary method consistent with the present disclosure.

FIG. 15 illustrates an exemplary method 2500 consistent with the principles of the present disclosure. Method 2500 may be performed and used by the robot system as disclosed above. Method 2500 may begin at step 2502 where the robot may import and store image data from a 3D imaging system and a 2D imaging system. The system may also store a 3D anatomical feature for a first coordinate system and a 2D anatomical feature for a second coordinate system. These imaging systems may be the same as described above and include a 3D CT scan and a 2D x-ray. In addition, the system may store placement information of a digital medical object on both the 3D and 2D images. At step 2504, certain features of the intra-op 2D images may be enhanced using image processing. At step 2506, the stored 3D image may undergo a rigid transformation to generate 2D DRR images (simulated 2D images) with volume orientation and location information in order to ultimately register the 3D image data to the intra-operative 2D image data. The volume and orientation information may be based upon the initial or subsequent iterations of the simulated 2D images depending on the results of a comparison that is described below.

At step 2508, features of the simulated 2D image data are enhanced using image processing and at step 2510 an initial feature of the simulated 2D image data may be compared to an image feature of the intra-operative 2D image feature. As a starting point for the comparison, the stored digital medical image from step 2502 may be used.

At step 2512, the system may determine if a match has occurred of the current feature of the simulated 2D image data and the image feature of the intra-operative 2D image data. If a match has occurred, method 2500 goes to step 2514 which registers the 3D coordinate system (first coordinate system) with the 2D coordinate system (second coordinate system). If a match does not occur at step 2512, method 2500 goes to step 2506 to compare a next iteration or another image feature of the simulated 2D image data to the image feature of the 2D image data. This repeats until a match has occurred, sending method 2500 to step 1514 to register the first and second coordinate systems.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

What is claimed is:

1. A surgical robot system comprising:
a robot having a robot arm and a robot base, wherein the robot base comprises an image registration facility configured to receive a three-dimensional (3D) medical image and a two-dimensional (2D) medical image; and
at least one camera configured to detect a one or more tracking markers in an anatomical coordinate system;
wherein the image registration facility is configured to generate a simulated 2D digital medical image from the 3D medical image and match the simulated 2D digital medical image to the 2D medical image,
wherein the image registration facility initially associates the simulated 2D digital medical image to the 2D digital medical image by corresponding a digital medical object placed on the 3D digital image with the digital medical object placed on the 2D digital medical image,
wherein the image registration facility is further configured to register by:
  (i) storing a 3D digital medical image comprising a 3D anatomical feature and a first coordinate system,
  (ii) storing a 2D digital medical image comprising a 2D anatomical feature and a second coordinate system,
  (iii) storing a placement of the digital medical object on the 3D digital medical image and the 2D digital medical image,
  (iv) generating a simulated 2D digital medical image from the 3D digital medical image, wherein the simulated 2D digital medical image comprises a simulated 2D anatomical feature corresponding to the 3D anatomical feature,
  (v) comparing the 2D anatomical feature with the simulated 2D anatomical feature until a match is reached, and
  (vi) registering the first coordinate system with the second coordinate system based on the match,
wherein the position of the robot arm and a position of the patient, using the one or more tracking markers, in the anatomical coordinate system is represented on a display depicting the first coordinate system,
wherein the robot arm is coupled to an end effector, the end effector being configured with one or more tracking markers on the surface of the end effector to be monitored when the end effector is translated and rotated in a surgical field
wherein the end effector includes a clamp configured to be a ground link and fasten the end effector to the robot arm,
wherein the robot arm includes a ring that is configured as a visual indicator to notify a user of different modes the system is operating under and configured to provide warnings to a user.

2. The system of claim 1, wherein the 3D digital image is generated by at least one of a computed tomography (CT) system and magnetic resonance imaging (MRI) system.

3. The system of claim 1, wherein the 2D digital image is generated by an x-ray system.

4. The system of claim 1, wherein the anatomical coordinate system is at least in part determined by an image tracking system that tracks the location of the patient.

5. The system of claim 1, wherein the 3D digital medical image is pre-operatively obtained from one of a tomography (CT) system and magnetic resonance imaging (MRI) system, and the 2D digital medical image is inter-operatively obtained from an x-ray system.

6. The system of claim 1, wherein the digital medical object is a surgical medical implant device.

7. The system of claim 1, wherein the digital medical object is at least one of a digitally-simulated bio-active implant device, electronics-based medical implant device, and artificial medical transplant material.

8. The system of claim 1, wherein the placement of the digital medical object appears as a shadow.

9. The system of claim 1, wherein the placement of the digital medical object provides a region of interest upon which the step of comparing begins.

10. The system of claim 1, wherein the placement of the corresponding digital medical object placed the 3D digital image and the acquired 2D digital medical image is provided with a placement tolerance.

11. The system of claim 1, wherein the match is determined within a matching tolerance.

12. A method for registration of digital medical image coordinate systems, comprising the steps of:
providing a robotic system having a robot arm and a robot base, wherein the robot base comprises an image registration facility configured to receive a three-dimensional (3D) medical image and a two-dimensional (2D) medical image;
storing a 3D digital medical image comprising a 3D anatomical feature and a first coordinate system;
storing a 2D digital medical image comprising a 2D anatomical feature and a second coordinate system;
storing a placement of a digital medical object on the 3D digital medical image and the 2D digital medical image;
generating a simulated 2D digital medical image from the 3D digital medical image, wherein the simulated 2D digital medical image comprises a simulated 2D anatomical feature corresponding to the 3D anatomical feature;
comparing the 2D anatomical feature with the simulated 2D anatomical feature until a match is reached; and
determining a registration of the first coordinate system with the second coordinate system based on the match
wherein the robot arm is coupled to an end effector, the end effector being configured with one or more tracking markers on the surface of the end effector to be monitored when the end effector is translated and rotated in a surgical field
wherein the end effector includes a clamp configured to be a ground link and fasten the end effector to the robot arm,
wherein the robot arm includes a ring that is configured as a visual indicator to notify a user of different modes the system is operating under and configured to provide warnings to a user.

13. The method of claim 12, wherein the 3D digital image is generated by at least one of a computed tomography (CT) system and magnetic resonance imaging (MRI) system.

14. The method of claim 12, wherein the 2D digital image is generated by an x-ray system and the second coordinate system is in reference to an anatomical coordinate system of a patient during a medical procedure.

15. The method of claim 14, wherein the anatomical coordinate system is at least in part determined by an image tracking system that tracks the location of the patient and the x-ray system.

16. The method of claim 12, wherein the 3D digital medical image is pre-operatively obtained from one of a tomography (CT) system and magnetic resonance imaging (MM) system, and the 2D digital medical image is inter-operatively obtained from an x-ray system.

17. The method of claim 12, wherein the digital medical object is a digitally-simulated surgical medical implant device.

18. The method of claim 12, wherein the digital medical object is at least one of a digitally-simulated bio-active implant device, electronics-based medical implant device, and artificial medical transplant material.

19. The method of claim 12, wherein the placement of the digital medical object appears as a replica of a real object on a medical image.

20. The method of claim 12, wherein the placement of the corresponding digital medical object placed the 3D digital image and the acquired 2D digital medical image is provided with a placement tolerance.

* * * * *